United States Patent
Carson et al.

(10) Patent No.: US 7,827,815 B2
(45) Date of Patent: Nov. 9, 2010

(54) APPARATUS AND METHOD FOR COOLING LIQUID IN INTRAVASCULAR COOLING SYSTEM

(75) Inventors: Gary A. Carson, Golden, CO (US); Marc E. Voorhees, Arvada, CO (US)

(73) Assignee: Medivance, Inc., Louisville, CO (US)

( * ) Notice: Subject to any disclaimer, the term of this patent is extended or adjusted under 35 U.S.C. 154(b) by 2 days.

(21) Appl. No.: 11/737,036

(22) Filed: Apr. 18, 2007

(65) Prior Publication Data

US 2007/0244475 A1 Oct. 18, 2007

Related U.S. Application Data

(60) Provisional application No. 60/793,164, filed on Apr. 18, 2006.

(51) Int. Cl.
*F25B 27/00* (2006.01)
(52) U.S. Cl. ............................... 62/238.3; 62/480
(58) Field of Classification Search ............ 62/94, 62/238.3, 259.3, 271, 371, 372, 480; 604/6.13, 604/82, 32, 65, 66, 113, 114, 248; 606/22; 607/96, 104, 105, 108, 113; 95/46, 241, 95/254; 206/439, 530, 535; 128/692, 713; 165/11 R, 46, 96
See application file for complete search history.

(56) References Cited

U.S. PATENT DOCUMENTS

| | | | |
|---|---|---|---|
| 3,212,286 A | | 10/1965 | Curtis |
| 3,734,293 A | | 5/1973 | Biskis |
| 4,161,210 A | * | 7/1979 | Reid et al. ............ 165/104.12 |
| 4,195,631 A | * | 4/1980 | Baucom ................... 604/6.04 |
| 4,444,727 A | | 4/1984 | Yanagihara et al. |
| 4,508,123 A | * | 4/1985 | Wyatt et al. ................ 600/505 |
| 4,580,408 A | | 4/1986 | Stuebner |
| 4,747,826 A | * | 5/1988 | Sassano ..................... 604/522 |
| 4,834,705 A | * | 5/1989 | Vaillancourt ................ 604/83 |
| 5,000,252 A | | 3/1991 | Faghri |
| 5,111,668 A | | 5/1992 | Parrish et al. |
| 5,113,666 A | | 5/1992 | Parrish et al. |
| 5,125,069 A | * | 6/1992 | O'Boyle ..................... 392/465 |
| 5,254,094 A | * | 10/1993 | Starkey et al. .............. 604/113 |
| 5,268,022 A | | 12/1993 | Garrett et al. |

(Continued)

FOREIGN PATENT DOCUMENTS

WO   PCT/US03/010311   10/2003

*Primary Examiner*—Mohammad M Ali
(74) *Attorney, Agent, or Firm*—Marsh Fischmann & Breyfogle LLP

(57) ABSTRACT

A portable apparatus and method for providing a cooled liquid for vascular administration are disclosed. The portable apparatus includes a source of liquid for vascular administration, a cooling reservoir for receiving liquid from the source, and a sorption-based heat exchanger for cooling liquid in the cooling reservoir by a sorption-based process. The heat exchanger may include an evaporative area for receiving and vaporizing a refrigerant, a sorptive material for sorping vaporized refrigerant, and a heat exchange member for conducting thermal energy from liquid in the cooling reservoir into the evaporative area. Additional componentry may be provided for fluidly interconnecting and controlling the flow of liquid from the source to the cooling reservoir and from the cooling reservoir to a vascular interface device. Such componentry may be conveniently packaged in a sterilized manner together with at least the cooling reservoir.

49 Claims, 13 Drawing Sheets

U.S. PATENT DOCUMENTS

| | | | |
|---|---|---|---|
| 5,289,695 A | | 3/1994 | Parrish et al. |
| 5,423,751 A | * | 6/1995 | Harrison et al. ............... 604/83 |
| 5,609,571 A | * | 3/1997 | Buckberg et al. .......... 604/6.13 |
| 5,624,477 A | | 4/1997 | Armond |
| 5,702,358 A | * | 12/1997 | Witherspoon et al. ........ 604/6.1 |
| 6,019,783 A | | 2/2000 | Philips et al. |
| 6,042,559 A | * | 3/2000 | Dobak, III ...................... 604/7 |
| 6,047,106 A | | 4/2000 | Salyer |
| 6,083,418 A | | 7/2000 | Czarnecki et al. |
| 6,257,011 B1 | | 7/2001 | Siman-Tov et al. |
| 6,349,560 B1 | * | 2/2002 | Maier-Laxhuber et al. . 62/457.9 |
| 6,364,937 B1 | | 4/2002 | McMahon |
| 6,389,839 B1 | | 5/2002 | Sabin |
| 6,436,130 B1 | * | 8/2002 | Philips et al. ............... 607/105 |
| 6,454,792 B1 | * | 9/2002 | Noda et al. ................. 607/105 |
| 6,463,212 B1 | | 10/2002 | Salyer |
| 6,503,297 B1 | | 1/2003 | Lu et al. |
| 6,508,859 B1 | * | 1/2003 | Zia et al. ....................... 95/46 |
| 6,559,096 B1 | | 5/2003 | Smith et al. |
| 6,584,797 B1 | | 7/2003 | Smith et al. |
| 6,591,630 B2 | | 7/2003 | Smith et al. |
| 6,601,404 B1 | | 8/2003 | Roderick |
| 6,688,132 B2 | | 2/2004 | Smith et al. |
| 6,701,724 B2 | * | 3/2004 | Smith et al. ................... 62/106 |
| 6,755,801 B2 | * | 6/2004 | Utterberg et al. ........... 604/4.01 |
| 6,858,068 B2 | | 2/2005 | Smith et al. |
| 6,878,156 B1 | | 4/2005 | Noda |
| 6,960,243 B1 | | 11/2005 | Smith et al. |
| 6,968,711 B2 | | 11/2005 | Smith et al. |
| 7,022,099 B2 | * | 4/2006 | Litzie et al. ................ 604/6.09 |
| 7,063,718 B2 | | 6/2006 | Dobak, III |
| 7,097,657 B2 | * | 8/2006 | Noda et al. .................. 607/105 |
| 7,172,586 B1 | | 2/2007 | Dae et al. |
| 2003/0150232 A1 | | 8/2003 | Brudnicki |
| 2004/0039344 A1 | * | 2/2004 | Baldwin et al. ............. 604/209 |
| 2006/0030916 A1 | | 2/2006 | Lennox |
| 2006/0074469 A1 | | 4/2006 | Lennox et al. |
| 2006/0124141 A1 | | 6/2006 | Dobak, III |
| 2006/0136023 A1 | | 6/2006 | Dobak, III |
| 2006/0161232 A1 | | 7/2006 | Kasza et al. |
| 2006/0247744 A1 | | 11/2006 | Nest et al. |
| 2006/0287697 A1 | | 12/2006 | Lennox |
| 2007/0043409 A1 | | 2/2007 | Brian, III et al. |

* cited by examiner

APPARATUS AND METHOD FOR COOLING LIQUID IN INTRAVASCULAR COOLING SYSTEM

CROSS-REFERENCE TO RELATED APPLICATIONS

This application claims priority to U.S. Patent Provisional Application Ser. No. 60/793,164 filed Apr. 18, 2006, entitled "APPARATUS AND METHOD FOR COOLING LIQUID IN INTRAVASCULAR COOLING SYSTEM". The foregoing patent application is incorporated herein by reference in its entirely.

FIELD OF THE INVENTION

The present invention relates to a portable apparatus and related method for rapid vascular cooling of a patient. The invention is particularly apt for treating stroke, head trauma and cardiac arrest patients in an ambulatory vehicle.

BACKGROUND OF THE INVENTION

The therapeutic use of rapid bodily cooling systems is ever-increasing. Of particular interest, it is now accepted that rapid cooling of stroke, cardiac arrest and head trauma patients can yield significant therapeutic benefits. Specifically, research indicates that even though a stroke or cardiac arrest victim's brain cells may lose their ability to function, the cells do not necessarily die quickly. In fact, brain damage from a stroke or cardiac arrest may take hours to reach maximum effect. Neurological damage may be reduced and the stroke or cardiac arrest victims' outcome improved if a neuroprotectant therapy is applied within this time frame.

Similarly, elements in the genesis of a traumatic brain injury (e.g., resulting from falls, vehicular accidents and the like) are now understood to overlap with elements in the genesis of neurological damage in stroke victims. In particular, delayed secondary injury at the cellular level after the initial head trauma is now recognized as a major contributing factor to the ultimate tissue loss that occurs after brain injury. Again, neurologic damage may be reduced if a neuroprotectant therapy is rapidly applied. Further, in this regard, studies have shown that treatment with mild hypothermia, defined as lowering core body temperature at 2-3° C. confers neuroprotection in stroke victims, and may hasten the neurologic recovery and improve outcomes when applied for 12-72 hours in cases of traumatic head injury. Again, to optimize such therapies, the neuro-protective therapy should be initiated as soon as possible after a stroke or traumatic head injury.

As these and other medical applications for rapid bodily cooling have continued to evolve, the present inventors have recognized the desirability of enhancing the portability, stowability and ease-of-use of patient cooling systems so that patient treatment may be promptly initiated. More particularly, while known patient cooling systems have proven effective for many applications, the present inventors have recognized that additional emergency-oriented applications can be realized via the implementation of further improved liquid cooling methodologies and stand-alone componentry, as well as enhanced componentry packaging. In this regard, the present inventors have recognized the need for a cooling system and related methodology that is particularly apt for use in ambulatory settings, including, in particular, use in emergency vehicles such as helicopters, ambulances and the like where space utilization is at a premium and patient access may be limited.

SUMMARY OF THE INVENTION

In view of the foregoing, a primary objective of the present invention is to provide a portable patient cooling system that reduces space storage and patient-site space requirements, is lightweight and yields highly effective patient cooling.

A further objective of the present invention is to provide an apparatus and method for patient cooling that is easy to set-up and is otherwise user-friendly.

Another objective of the present invention is to provide an on-demand patient cooling system that reduces or avoids the need for electrical or other on-board power utilities.

Another objective of the present invention is to provide an improved patient cooling apparatus and related method that is cost effective.

Yet another objective of the present invention is to provide an apparatus and method for patient cooling that is, at least in part, adapted for single patient use and ready disposal.

One or more of the above objectives and additional advantages may be realized in the present invention which includes a portable apparatus and associated method for providing a cooled liquid for vascular administration. The portable apparatus may include a source of liquid for vascular administration (e.g., one or more bags containing about 1 liter to 4 liters and preferably 1.5 liters to 3 liters of a saline solution, plasma solution, etc.), and a cooling reservoir for receiving liquid from the source. Additionally, the portable apparatus may include a sorption-based heat exchanger for cooling liquid in the cooling reservoir, wherein the sorption-based heat exchanger may include an evaporative area for receiving and vaporizing a refrigerant therein, a sorptive material for sorping vaporized refrigerant (e.g., a desiccant), and a heat exchange member for conducting thermal energy from the liquid in the cooling reservoir into the evaporative area, wherein the liquid received in the cooling reservoir may be rapidly cooled.

As will be appreciated, the employment of a sorption-based heat exchanger not only yields rapid cooling of a liquid for vascular administration, but also facilitates the realization of numerous additional benefits, including enhanced portability, stowability and on-demand liquid cooling. Further, the employment of a sorption-based heat exchanger avoids the need for electrical or other power requirements for liquid cooling.

In relation to cooling capabilities, the inventive apparatus may cool liquid at a rate sufficient to lower a patient's core temperature by 0.5° C. to 4° C., and preferably 1° C. to 2° C., over a cooled liquid infusion period of 15 minutes to 60 minutes, and preferably 20 minutes to 30 minutes. Characterized another way, the inventive apparatus may yield a total energy transfer of 7 kcal to 104 kcal and preferably 19.5 kcal to 60 kcal.

In another aspect, the cooling reservoir of the inventive apparatus may comprise an inlet for receiving liquid from the source and an outlet for passing liquid out of the cooling reservoir, and at least one flow channel for flowing the liquid between the inlet and outlet. Such an arrangement facilitates the overlapping flow of liquid into and out of the cooling reservoir, e.g., as opposed to a sequential flow protocol. In this regard, when a liquid is flowed into the cooling reservoir inlet at a temperature of 15° C. to 30° C., and preferably 20° C. to 25° C., such liquid may be sufficiently cooled to an outlet temperature of 2° C. to 8° C., and preferably 5° C. to 7° C., thereby yielding a liquid temperature drop of 7° C. to 26°, and preferably 13° C. to 20° C., within the cooling reservoir.

The inlet may be located at a location on the cooling reservoir that is disposed below the outlet during use (e.g., an inlet at a bottom end and an outlet near a top end), so as to facilitate the removal of any gaseous bubbles in the cooled liquid (e.g., removal by an optional gas removal device discussed below). Preferably, a plurality of flow channels may extend between the inlet and outlet of the cooling reservoir, so as to equalize thermal transfer between the heat exchange member and cooling reservoir (e.g., by reducing low flow regions in the cooling reservoir). In this regard, at least a portion of each of the plurality of flow channels may be disposed to extend adjacent to the heat exchange member of the sorption-based heat exchanger for thermal conduction therebetween. More specifically, at least a portion of each of the flow channels may extend substantially parallel to a corresponding surface portion of the heat exchange member. In one arrangement, one or more of the flow channels may be disposed to define a non-linear path between the inlet and outlet of the cooling reservoir, thereby increasing the degree of achievable cooling for liquid passing therethrough.

In another aspect, the cooling reservoir may be provided so as to define a sterile internal volume for receiving and transferring liquid from the source. In this regard, the apparatus may be provided to include a sterile first liquid flow line (e.g., flexible tubing) fluidly interconnected or fluidly interconnectable between the source and the cooling reservoir, and a sterile second liquid flow line (e.g., flexible tubing) fluidly interconnected or fluidly interconnectable between the reservoir and a vascular interface device (e.g., vascular catheter). Further, the apparatus may include an enclosure for containing, in a sterile, enclosed area, at least the cooling reservoir, the first liquid flow line and the second liquid flow line prior to use. Such an arrangement facilitates shipping, stowability and ready set-up/use. Further, such an approach allows sterile packaging to be reliably completed at a production location.

Optionally, additional liquid flow componentry may be advantageously provided or otherwise employed together with the cooling reservoir and first and second liquid flow lines. In particular, at least one flow control member may be provided to allow for control over the initiation/termination and rate of liquid flow into and out of the cooling reservoir. For example, a flow control member may be provided for contact engagement with the first liquid flow line (e.g., interconnected for selective occlusive engagement therewith) or second liquid flow line. Alternatively, a flow control member may be provided for flow control use either upstream and/or downstream of the first and/or second liquid flow lines. Further, a gas removal device may be provided to remove gaseous bubbles from liquid flowing to a patient. For example, a gas removal device may be disposed along the first or second liquid flow line (e.g., fluidly interconnected in-line therewith) or downstream thereof. Additionally, a source interconnection member (e.g., a bag spike with a removable cover) may be provided at one end of the first liquid flow line for ready connection to the vascular cooling liquid source, and a vascular interconnection member may be provided (e.g., a luer connector with a removable cap, a spikeable tubing length or a twist-off spikeable port) may be provided at one end of the second liquid flow line for ready interconnection to a vascular access device (e.g., having a vascular catheter fluidly interconnected or interconnected to a patient at one end and a compatible luer connector at another end). As may be appreciated, any/all of such flow componentry may be packaged in a sterile condition separately, or together with the noted cooling reservoir and liquid flow lines to further facilitate storage and ready use.

In yet a further aspect, the apparatus may include a flow pump device for pumping liquid from the vascular liquid source and into/out of the cooling reservoir. More particularly, the flow pump device may be operable to maintain a predetermined flow rate, e.g., preferably between about 50 ml./min. and 100 ml./min. In preferred arrangements, the flow pump device may be of a mechanical nature so as to avoid the need for electrical or other power sources. For example, a manually inflatable bladder device (e.g., inflatable via a hand-operated, valved pump) may be utilized to apply a compressive force against a flexible vascular liquid source so as to displace liquid from the source at a predetermined rate.

In one arrangement, the cooling reservoir may be provided so as to be removably positionable adjacent to the heat exchange member of the sorption-based heat exchanger. For example, the cooling reservoir may be configured (e.g., a laminar configuration) for convenient slide-in/slide-out placement in a coincidentally-configured receiving slot (e.g., vertically oriented) provided on the sorption-based heat exchanger. Such an approach facilitates reuse of the sorption-based heat exchanger and ready removal/separate disposal of the cooling reservoir after use. In another approach, the reservoir may be fixedly positioned adjacent to the heat exchange member of the sorption-based heat exchanger. Such approach further facilitates initial set up procedures, and yields an arrangement in which the cooling reservoir and sorption-based heat exchanger may be packaged/stowed together and disposed of together after use.

In yet a further aspect, the cooling reservoir may be provided to be either removably positionable or fixedly positioned in direct contact with a first side of the heat exchange member of the sorption-based heat exchanger, wherein the evaporative area and sorptive material are located on an opposing second side of the heat exchange member of the sorption-based heat exchanger. In turn, the evaporative area and sorptive material may be located within an enclosed volume of the sorption-based heat exchanger. In conjunction with this aspect, the portable apparatus may further include a vessel containing a refrigerant (e.g., a liquid refrigerant comprising water), and an actuator selectively actuatable to fluidly interconnect and thereby flow the refrigerant from the vessel into the enclosed volume. The enclosed volume of the sorption-based heat exchanger may be maintained at internal pressure that is less than an internal pressure of the vessel prior to fluid interconnection. In this regard, the enclosed volume may be maintained at a predetermined subatmospheric pressure prior to and after activation. By way of example, the predetermined subatmospheric pressure may be less than about 5 hectopascals (hPa) and most preferably less than about 2 hPa.

In one arrangement, the vessel and actuator may be provided as part of the sorption-based heat exchanger. In other arrangements, the vessel and actuator may be separately disposed with a fluid interconnection to the sorption-based heat exchanger. In one embodiment, the actuator may comprise a depressible member for puncturing the refrigerant vessel so as to allow liquid refrigerant to flow into the evaporative area. that is, for example, a user may simply push in on one end of the depressible member thereby causing another end thereof to breach a refrigerant vessel that is contained within another vessel fluidly interconnected to the evaporative area. The inclusion of a selectively actuatable actuator for the sorption-based heat exchanger further facilitates the provision of an on-demand, portable cooling solution.

In one arrangement, the refrigerant vessel may be partially defined by a flexible surface that is disposed for exposure to atmospheric pressure, wherein upon the selective actuation of the actuator, a flow path is defined between the vessel and the enclosed volume of the sorption-based heat exchanger that is maintained at subatmospheric pressure. The pressure differential facilitates the flow of liquid from the refrigerant vessel into the evaporative area. As may be appreciated, such an arrangement further facilitates the automatic passage of refrigerant from the vessel into the evaporative area.

In further relation to this aspect, the sorption-based heat exchanger may include a vapor permeable membrane, which is disposed between the heat exchange member/evaporative area and sorptive material within the enclosed volume (e.g., disposed parallel to the heat exchange member to define the evaporative area therebetween). In this regard, the vapor permeable membrane functions to restrict the passage of refrigerant in the evaporative area to that which has been vaporized, e.g., as opposed to refrigerant in a liquid form.

The heat exchange member may comprise any material that allows for thermal energy conduction between liquid in the cooling reservoir and the evaporative area. In one approach, the heat exchange member may comprise a metal (e.g., an aluminum plate), thereby facilitating thermal energy transfer and also yielding structural integrity.

In some embodiments at least one distribution member may be provided with the vapor permeable membrane to facilitate distribution of refrigerant flowing into the evaporative area. In one approach, a porous wicking member may be positioned between a front side of the heat exchange member and a backside of the vapor permeable member. By way of example, the porous wicking member may extend for at least a majority of the length of the vapor permeable membrane and may have a portion that is positioned adjacent to an inlet through which liquid refrigerant passes from the vessel into the evaporative area. In another approach, a vapor impermeable member may be positioned adjacent to a front side of the vapor permeable membrane. For example, the vapor impermeable membrane may extend for at least a majority of the length of the vapor permeable membrane and may have a portion that is positioned adjacent to an inlet through which liquid refrigerant passes from the vessel into the evaporative area. The distribution members described above may be employed separately or in tandem.

Additionally, the sorption-based heat exchanger may comprise at least one spacer member extending through the sorptive material to define at least one corresponding channel region for receiving vaporized refrigerant therethrough. More preferably, a plurality of spacer members are provided so as to provide for enhanced contact between vaporized refrigerant and sorptive material. In turn, such increased contact yields increased/efficient liquid cooling capabilities, thereby facilitating rapid patient cooling.

Relatedly, the sorption-based heat exchanger may be provided to include a phase change material (e.g., a hydrated salt or paraffin-based material) for extracting thermal energy attendant to sorption of the vaporized refrigerant by the sorptive material. In this regard, it is preferable that at least a portion of the phase change material be located directly adjacent to at least a portion of the sorptive material. By way of example, a plurality of spacer members may be disposed transversely (e.g., perpendicular) to the evaporative area, with sorptive material adjacent to each side of each spacer member and phase change material disposed therebetween (e.g., to yield a multi-layered, laminar arrangement).

In one arrangement, the sorption-based heat exchanger may also include a porous insulation layer disposed between the vapor permeable membrane and the sorptive material (e.g., disposed in parallel relation to the heat exchange member and vapor permeable member).

As noted, the present invention also provides an inventive method for supplying a cooled liquid for vascular administration. The inventive method may include the steps of flowing a liquid for vascular administration from a source into a cooling reservoir, conducting thermal energy from the liquid in the cooling reservoir into an evaporative area of a sorption-based heat exchanger, and passing cooled liquid from the cooling reservoir to a vascular interface device. As may be appreciated, the conduction of thermal energy may be realized via vaporization of a refrigerant within the evaporative area, wherein the vaporized refrigerant is sorped by a sorptive material within the sorption-based heat exchanger.

In one aspect of the inventive method, the conduction of thermal energy may act to cool liquid within the cooling reservoir between about 7° C. and 26° C., and preferably between about 13° C. and 20° C., relative to a starting temperature of the liquid within a source (e.g., a saline solution having a temperature of between about 15° C. and 30° C. and preferably 20° C. to 25° C., in a bag). In a related aspect, upon passing the cooled liquid from the cooling reservoir to a vascular interface device, the cooled liquid may be administered to a patient, wherein the cooled liquid acts to cool the patient between about 0.5° C. and 4° C., and preferably between about 1° C. and 2° C. (e.g., over a period of about 15 minutes to 60 minutes, preferably 20 minutes to 30 minutes). Characterized in another way, in conducting thermal energy from the liquid, a total transfer of between about 7 kcal and 104 kcal of thermal energy may be realized, and preferably between about 14.5 kcal and 60 kcal.

In a further related aspect, the evaporative area of the sorption-based heat exchanger may be located within the enclosed volume. In turn, the inventive method may provide for restricting the passage of refrigerant in a liquid form from the evaporative area, i.e., so as to permit substantially only vaporized refrigerant to contact the sorptive material. By way of primary example, such restriction may be achieved by locating a vapor permeable membrane between the evaporative area and the sorptive material.

In an additional aspect, the conduction of thermal energy into the evaporative area may be initiated by selectively introducing the refrigerant in a liquid form into the evaporative area. More particularly, such selective introduction may entail flowing of the liquid refrigerant from a vessel into the evaporative area by selectively fluidly interconnecting the vessel and evaporative areas, e.g. by manual depression of an actuator and/or by utilizing atmospheric pressure acting upon a flexible side of the vessel. Further in this regard, the enclosed volume of the sorption-based heat exchange may be maintained at an internal pressure less than an internal pressure of the liquid refrigerant vessel, wherein upon actuating an actuator, liquid refrigerant may flow from the vessel into and vaporize within the evaporative area. In one approach, the enclosed volume may be maintained at a subatmospheric pressure of less than about 5 hectopascal (hPa), and preferably less than about 2 hPa prior to and after actuation.

In another aspect, sorption of the vaporized refrigerant by the sorptive material may be carried out by contacting the vaporized refrigerant with the sorptive material within the enclosed volume of the sorption-based heat exchanger (e.g., to condense the vapor on the sorptive material). In a related aspect, thermal energy released by the sorptive material upon sorption of the vaporized refrigerant may be extracted within the enclosed volume by a phase-change material. By way of example, the extracting step may comprise extracting thermal energy generated by the sorption material during sorption by utilizing a phase-change material having a solid to liquid transition temperature of from about 10° C. to 80° C.

In yet a further aspect, the method may comprise the steps of interconnecting the source for liquid administration to the cooling reservoir via a first flow line prior to the flowing step, and connecting the cooling reservoir to a vascular interface device prior to the flowing step. Further, the flowing step may entail pumping the liquid through the first liquid flow line of the cooling reservoir and second liquid flow line. By way of example, and as noted above, such pumping may be achieved by utilization of a manual pumping device, e.g., an inflatable bladder device that is hand-operated (e.g. by squeezing a flexible, valved chamber to inflate the bladder device).

In a related aspect, interconnection of the vascular liquid source to the cooling reservoir may be accomplished by manually connecting an interconnection member provided at one end of the first liquid flow line to the source, wherein a second end of the first liquid flow line is one of interconnected and adapted for interconnection to the reservoir. Similarly, fluid interconnection of the reservoir to a vascular interface device may entail a manual connection of an interconnection member at one end of the second liquid flow line to a vascular interface device (e.g., a vascular catheter), wherein a second end of the second liquid flow line is one of interconnected and adapted for interconnection to said reservoir.

In a further aspect, the method may include the step of controlling a flow control device to control the flow of liquid from the source through the cooling reservoir. More particularly, the controlling step may provide for initiating/stopping the flow of liquid and/or otherwise controlling the rate of flow of liquid through the first liquid flow line and/or second liquid flow line. In one arrangement, the controlling step may include manual adjustment of a flow control device that engages a first liquid flow line or a second liquid flow line so as to control a degree of occlusion of the first liquid flow line to effect the rate of liquid flow therethrough. In another arrangement, a flow control device may be utilized downstream of a second liquid flow line.

In an additional aspect, the method may further comprise the step of removing gas from liquid flowing through the first liquid flow line and/or the second liquid flow line. By way of example, such removing step may accomplish by passing the liquid in the second liquid flow line through a vented drip chamber disposed along and fluidly interconnected with the second liquid flow line (e.g., having a hydrophobic membrane to permit the passage of gas and restrict the passage of liquid therethrough).

In addition to the foregoing aspects, the method may further include the step of packaging the reservoir, first liquid flow line and second liquid flow line in a sterile enclosure. Further, such packaging step may provide for inclusion of a first interconnection member interconnected or interconnectable to one end of a first liquid flow line, a second interconnection interconnected or interconnectable to one end of the second liquid flow line, a flow control device as noted above and/or a gas removal device as noted above in the sterile enclosure. Further, in arrangements where the reservoir is fixedly interconnected with a sorption-based heat exchanger, the packaging step may provide for the further inclusion of the sorption-based heat exchanger within the sterile envelope.

In conjunction with this aspect, the packaging step may be efficiently completed at a production location. In this regard, the various componentry may be sterilized before packaging or collectively sterilized after packaging. Relatedly, then the method may entail the additional step of unpackaging the various components packaged in the sterile enclosure at a patient care site remote from the production site. By way of example, such patient care site may be within an ambulatory vehicle.

In conjunction with the above-noted aspect relating to the various componentry interconnections, the method may further provide for disconnection of the second connection member from the vascular interface device, and single-step disposal of interconnected ones of the second interconnection member, second liquid flow line, cooling reservoir, first interconnection member and source in a joint fashion.

Additional aspects and advantages of the present invention will become apparent to those skilled in the art upon consideration of the Detailed Description and claims that follow.

DETAILED DESCRIPTION OF THE INVENTION

Figure 1:
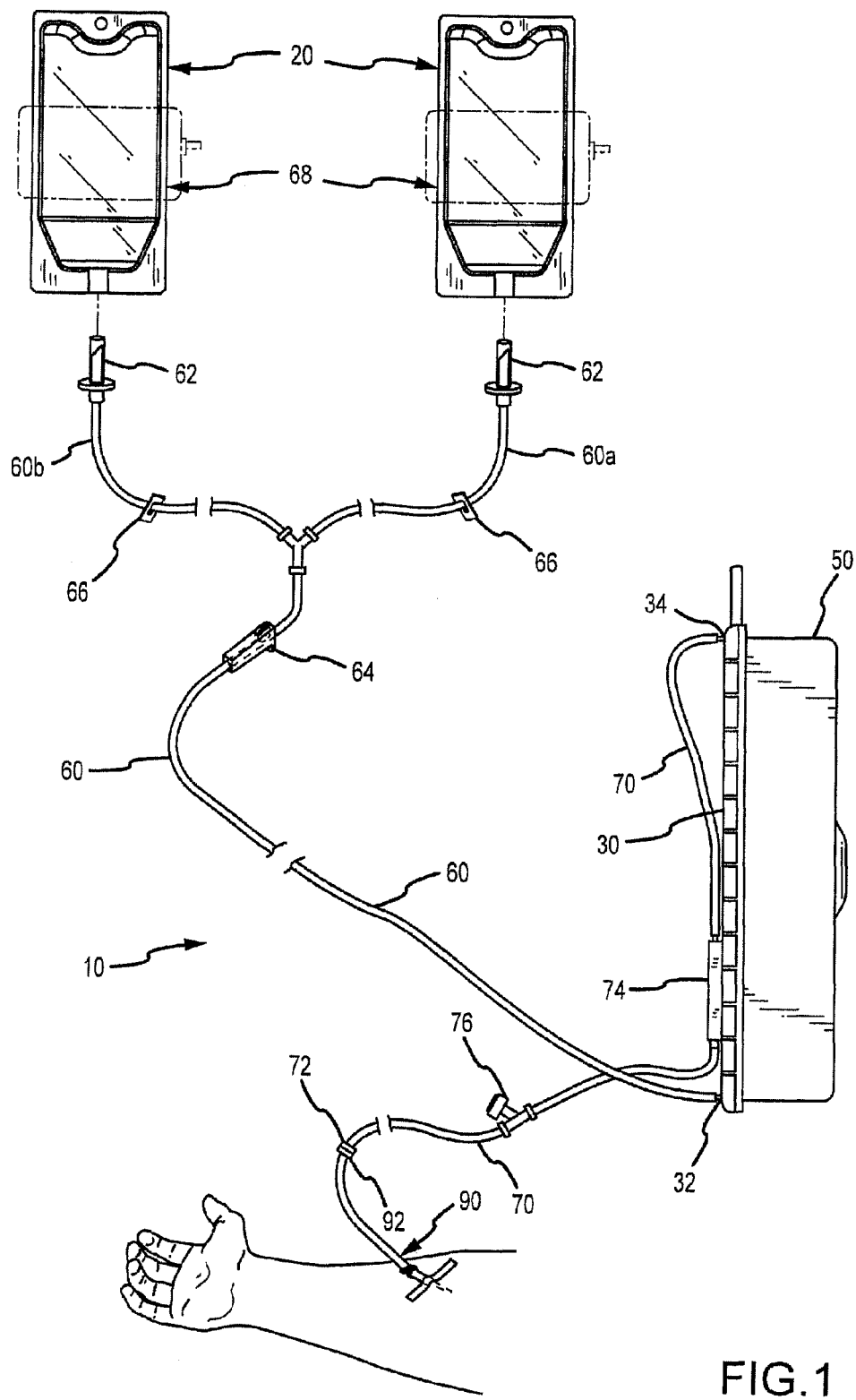
FIG. 1 illustrates one embodiment of an inventive portable apparatus for providing a cooled liquid for vascular administration.

FIG. 1 illustrates one embodiment of a portable apparatus 10 for cooling a liquid for vascular administration. As shown, the portable apparatus 10 may include at least one source reservoir(s) 20 containing a liquid appropriate for cooling a patient via vascular administration. By way of example, the source reservoir(s) 20 may contain a predetermined volume of a saline solution, plasma solution, or other solution, e.g., preferably about 1 liter to 4 liters of a saline solution, and more between about 1.5 liters to 3 liters of a saline solution. As may be appreciated, bags of saline solution are frequently otherwise kept within ambulatory vehicles for vascular administration and may be conveniently utilized.

The portable apparatus 10 may further include a cooling reservoir 30 for receiving liquid from source reservoir(s) 20 and a sorption-based heat exchanger 50 for cooling liquid received in the cooling reservoir 30. In one approach, the cooling reservoir 30 may be removably positionable relative to the sorption-based heat exchanger 50 for conductive thermal transfer therebetween (e.g., in a slot configured for matingly receiving the cooling reservoir 30), wherein the cooling reservoir 30 is separately disposable to facilitate reuse of the sorption-based heat exchanger 50. In another approach, the cooling reservoir 30 may be fixedly positioned relative to the sorption-based heat exchanger 50 for conductive thermal transfer therebetween, wherein the cooling reservoir 30 and the sorption-based heat exchanger 50 may be conveniently packaged and disposed of as a unit, and wherein set-up procedures may be expedited.

In either approach, it is preferable to define an arrangement in which a predetermined amount of total energy is transferable between sorption-based heat exchanger 50 and liquid from source reservoir(s) 20 flowing into and out of cooling reservoir 30, e.g., between about 20 kcal and 80 kcal, and more preferably between about 30 kcal and 60 kcal. Relatedly, it may be preferable to provide a portable apparatus 10 capable of cooling liquid from source reservoir(s) 20 so as to lower a patient's core temperature by 0.5° C. to 4° C., and preferably 1° C. to 2° C., during vascular cooling (e.g., over a period of about 15 to 60 minutes and preferably 20 minutes to 30 minutes).

Various additional flow componentry may be interconnected and/or readily interconnectable "upstream" between the source reservoir(s) 20 and cooling reservoir 30, and "downstream" of the cooling reservoir 30. For example, the upstream and downstream components may include a first liquid flow line 60 and a second liquid flow line 70 (e.g., flexible tubing lines having a bore size of between about 0.8 mm and 3 mm), respectively, each interconnected or interconnectable to cooling reservoir 30. More particularly, in the illustrated embodiment, the first liquid flow line 60 may be fluidly interconnected or interconnectable at a first end to an inlet port 32 of the cooling reservoir 30. Further, the first liquid flow line 60 may selectively be interconnectable at a second end to the source reservoir(s) 20. In the latter regard, at least one interconnection member 62 may be provided at the second end of the first liquid flow line 60 for selective fluid interconnection to the source reservoir(s) 20. By way of example, the interconnection member 62 may be a bag spike having a vented cap as shown, or may otherwise be defined by a lure connector or any other type of connector adapted for ready fluid interconnection with source reservoir(s) 20.

In the illustrated embodiment, a first flow control member 64 may be included along the length of the first liquid flow line 60 for controlling the flow of liquid through the first liquid flow line 60 to cooling reservoir 30. By way of example, first flow control member 64 may be a roller clamp that depressibly engages, and thereby occludes, a flexible first liquid flow line 60 to control the rate of liquid flow therethrough. Additionally, a second liquid flow control member 66 may be disposed along the length of the first liquid flow line 60 to control the flow of liquid therethrough. For example, the second liquid flow control member 66 may take the form of a slide clamp having a central opening with a v-shaped portion for progressively receiving and thereby occluding a flexible first liquid flow line 60 therein.

In addition to the noted flow components, a flow pump device 68 may be provided for pumping liquid from the source reservoir(s) 20. That is, the flow pump device 68 may be provided to flow liquid from the source reservoir(s) 20 and into and out of the cooling reservoir 30 at a predetermined rate, e.g., between about 20 ml./min. to 200 ml./min., and more preferable between about 50 ml./min. and 100 ml./min. Relatedly, it may be preferable to provide flow pump device 68 and cooling reservoir 30 so that the liquid pressure drop from first liquid flow line 60 to second liquid flow line 70 is less than about 80 mmHg. and more preferably less than about 30 mmHg.

While automated pumping devices may be utilized, FIG. 1 illustrates an embodiment in which the flow pump device 68 is defined by an inflatable bladder that is readily positionable around or otherwise in contact with at least a portion of a flexible cooling reservoir 30 to apply a compressive force thereto when inflated. By way of example, an inflatable bladder of the type marketed by Ethox Corp., of Buffalo, N.Y., U.S., under the trade name INFU-SURG® may be utilized. Such device comprises a valved, hand-squeezable pump for drawing in ambient air and dispensing the air into an inflatable bladder. As may be appreciated, the utilization of an inflatable bladder to provide a motive force for flowing liquid from the source reservoir(s) 20 reduces on-board power requirements and otherwise yields space efficiencies, stowability benefits, and reduced costs.

At this point, it should be noted that FIG. 1 illustrates the utilization of plural source reservoir(s) 20 so as to increase the total volume of liquid available for vascular administration to a patient. Specifically, two source reservoir(s) 20 are provided (e.g., each containing 1 l. of saline solution), and concomitantly a first liquid flow line 60 is provided with first and second spur lines 60a and 60b that are fluidly interconnected via a Y-connector 69. Correspondingly, each of the spur lines 60a, 60b are provided with a corresponding second flow control member 66 and interconnection member 62 (e.g., bag spikes). Further, separate flow pump devices 68 may be utilized in relation to each of the source reservoir(s) 20.

As further shown in FIG. 1, a first end of the second flow line 70 may be fluidly interconnected to an outlet port 34 of the cooling reservoir 30 and a second end of the second liquid flow line 70 may be fluidly interconnectable to an intravascular access device 90. Such intravascular access device 90 may comprise a vascular catheter fluidly interconnected to a female luer 92. In this regard, an interconnection member 72 may be provided at the second end of the second liquid flow line 70 for selective fluid interconnection to the vascular access device 90. By way of example, the interconnection member 72 may take the form of a male luer that is initially provided with a removable cap to maintain sterility.

In an illustrated embodiment, a gas removal device 74 may be included along the length of the second liquid flow line 70 for removing gas from the liquid flowing through the second liquid flow line 70 from reservoir 30. By way of example, the gas removal device 74 may be a vented drip chamber. Additionally, a medication administration port member 76 may be disposed along the second liquid flow line 70 to allow for the selective introduction of a medication into the second liquid flow line 70.

As may be appreciated, the various flow components interconnected and/or interconnectable to the first liquid flow line 60 and second liquid flow line 70 may be sterilized and packaged together with cooling reservoir 30. Such consolidated packaging facilitates sterilization procedures, transport and storage in emergency patient transport vehicles, and otherwise facilitates rapid set-up procedures. In this regard, such componentry may be readily removed from the sterile packaging, interconnected to source reservoir(s) 20 and an intravascular access device 90 for patient cooling.

In a simplified arrangement, a portable apparatus may simply comprise a sorption-based heat exchanger 50, a cooling reservoir 30, and a first liquid flow line 60 and a second liquid flow line 70 interconnectable to an inlet port 32 and outlet port 34, respectively, of the cooling reservoir 30. An interconnection member 62 (e.g., bag spike) may be provided at one free end of the first liquid flow line 60 and another interconnection member 72 (e.g., a spikeable tubing section) may be provided at one end of the second liquid flow line 70 for selective fluid interconnection with a separately provided intravascular tubing set. In the latter regard, the interconnectable intravascular tubing set may include a compatible interconnection member (for example, a spike) at one end, a gas removal device (e.g., a vented bubble trap), a flow control member (e.g., a roller clamp), and an optional drug introduction member interconnected along the length of a tubing line and a luer connector at a free end for selective interconnection to an intravascular access device. Of note, the various above-noted components of the portable apparatus can be packaged together in one sterile enclosure and the components of the interconnected intravascular tubing set may be packaged together in another sterile enclosure.

Figure 2A:
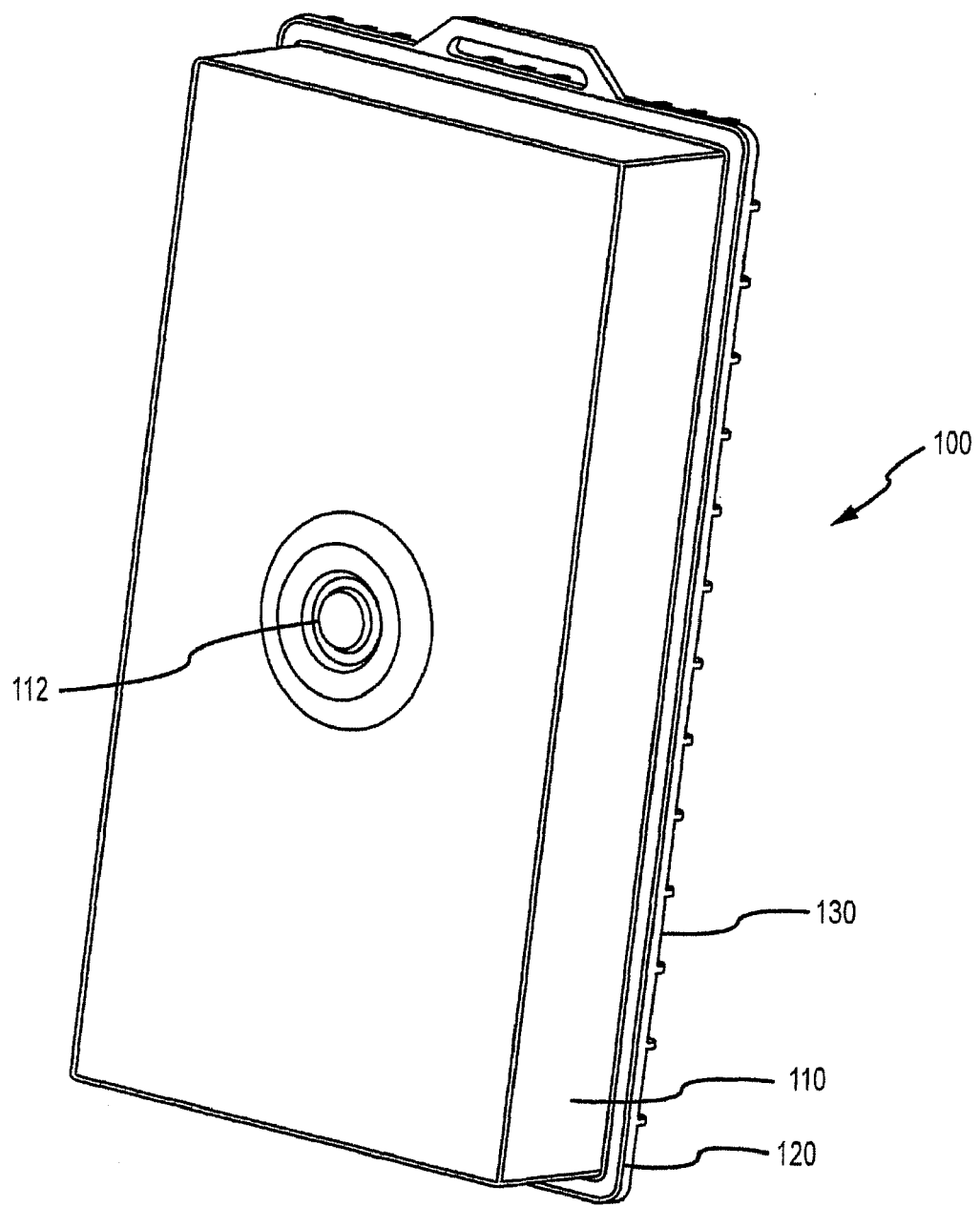
FIG. 2A illustrates a front perspective view of one embodiment of a sorption-based heat exchanger and adjacently-disposed cooling reservoir comprising the present invention.

Referring now to FIGS. 2A-2D, one embodiment of a sorption-based heat exchanger 100 will be described. As shown in FIG. 2A, the sorption-based heat exchanger 100 includes a housing member 110 interconnected to a front side of a heat exchange member 120 to define an enclosed volume therebetween. For example, a peripheral edge of housing member 110 may be fixedly sealed (e.g., via a light-activated adhesive) to a peripheral rim portion of the front side of heat exchange member 120. In this embodiment, a cooling reservoir 130 is fixedly interconnected to an opposing, backside of the heat exchange member 120. For example, a peripheral edge of cooling reservoir 130 may be fixedly sealed (e.g., via a light-activated adhesive) to a peripheral rim portion of the back side of heat exchange member 120.

Figure 2B:
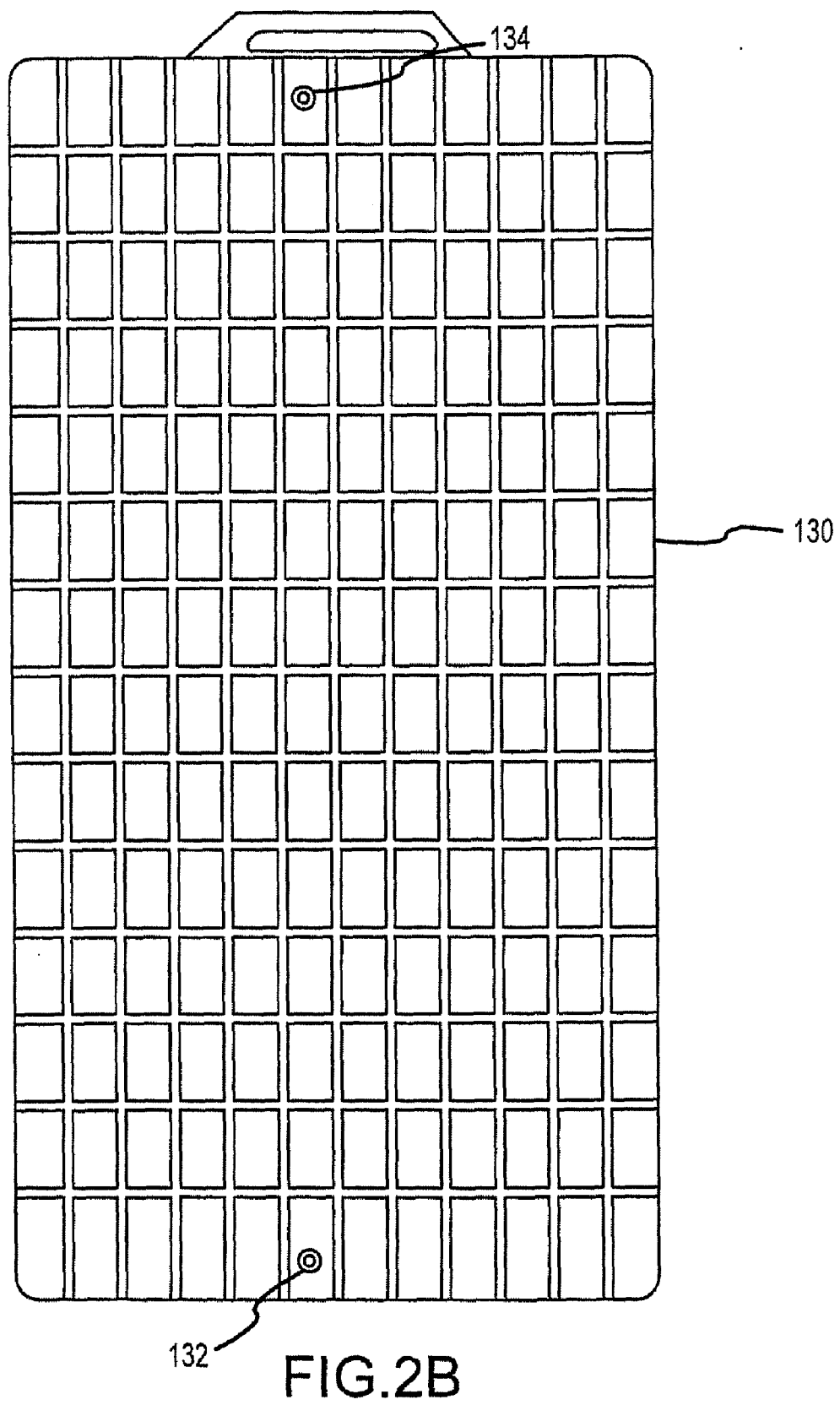
FIG. 2B illustrates a rear view of the cooling reservoir of the embodiment of FIG. 2A.

Upon selective actuation of an actuator 112 the sorption-based heat exchanger 100 provides for the selective vaporization of a liquid refrigerant within the enclosed volume on the first side of the heat exchange member 120, wherein thermal energy is conducted from liquid received within the cooling reservoir 130 from a source reservoir(s) 20 to cool the liquid. To yield high conduction cooling and otherwise provide structural rigidity the heat exchange member 120 may comprise a metallic material, e.g., aluminum, having a thickness of about 0.25 mm to 2 mm and preferably about 0.5 mm to 1 mm. In the latter regard, and as shown in FIG. 2B, the cooling reservoir 130 includes a bottom inlet port 132 and top outlet port 134 fluidly interconnectable or otherwise interconnected to first and second liquid flow lines 60 and 70, respectively, wherein liquid flows through the reservoir 130 from bottom to top to facilitate gas removal by a downstream or upstream gas removal device. In another arrangement, the location of ports 132 and 134 may be reversed, wherein liquid flows through the reservoir 130 from top to bottom.

Figure 2C:
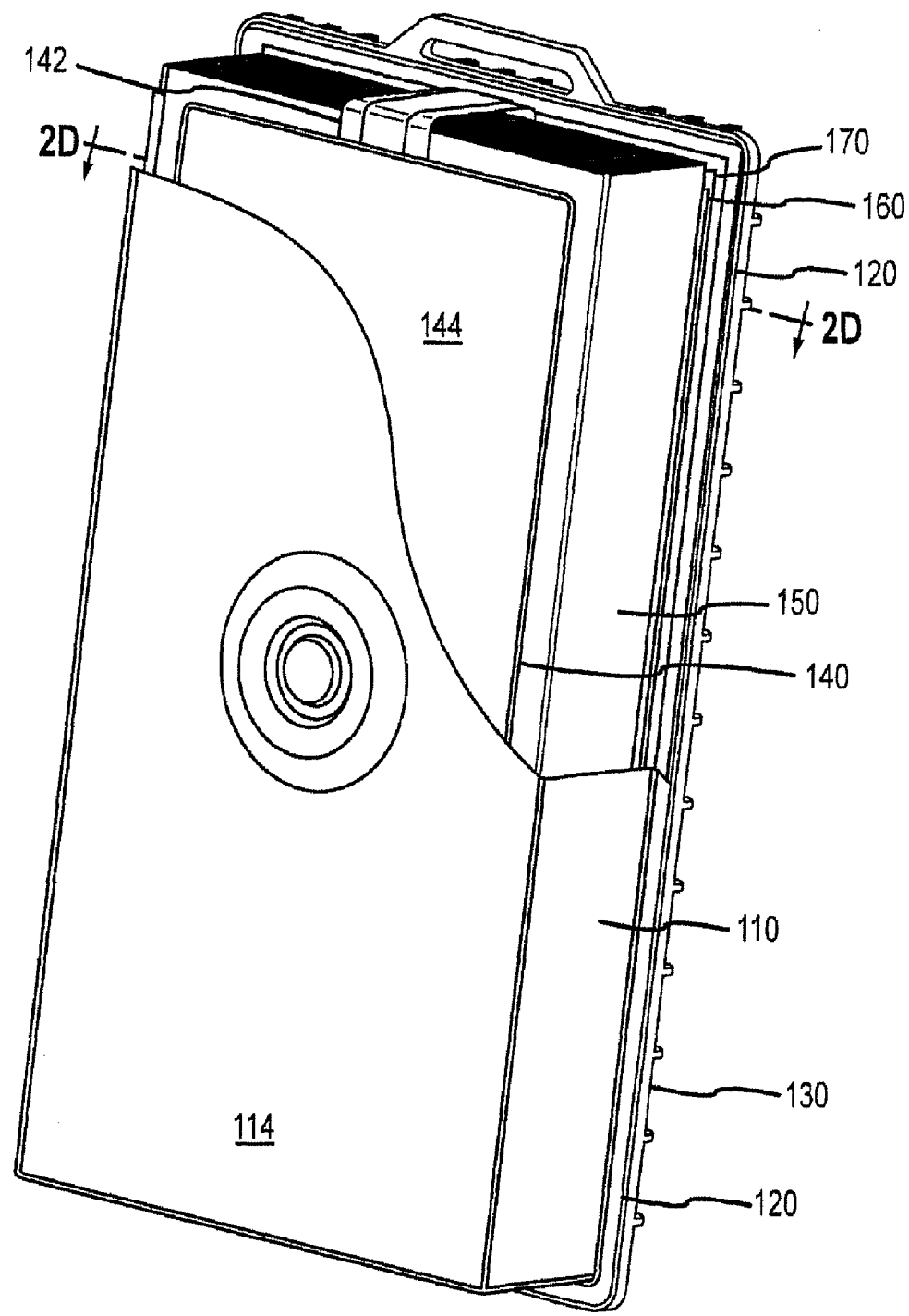
FIG. 2C illustrates a front perspective view of the embodiment of FIG. 2A, with a portion of a housing member cut away to show internally-disposed componentry.

Referring now to FIG. 2C, the sorption-based heat exchanger 100 is illustrated with a portion of the housing member 110 cut away to show components disposed within the enclosed volume thereof. As illustrated, such componentry is arranged in a front-to-back layered manner. In particular, the sorption-based heat exchanger 100 includes a liquid refrigerant vessel 140, a sorption layer 150, a thermal insulation layer 160, and a vapor permeable membrane 170 adjacently disposed in a laminar fashion on the front side of the heat exchange member 120.

The liquid refrigerant vessel 140 may interface with the actuator 112 of housing member 110 so that, upon selective depression of the actuator 112 by a user, a flow path is defined from the liquid refrigerant vessel 140 into an evaporative area located between a back side of the vapor permeable membrane 170 and front side of the heat exchange member 120. More particularly, the liquid refrigerant vessel 140 may comprise an inner pouch containing a liquid refrigerant and an outer pouch having top and bottom flow bands 142 that have open passageways therethrough with open port ends that are fluidly interconnected with the noted evaporative area through corresponding openings in vapor permeable membrane 170.

In the latter regard, vapor permeable membrane 170 may be provided to have a vaporized liquid refrigerant transmission rate of between about 4800 g/m$^2$/day and 290,000 g/m$^2$/day, and more preferably between about 21,000 g/m$^2$/day and 111,000 g/m$^2$/day. In this regard, vapor permeable membrane 170 may be preferably define a surface area for vaporized liquid refrigerant transmission of between about 400 cm$^2$ and 1,200 cm$^2$, and preferably between about 300 cm$^2$ and 800 cm$^2$. The vapor permeable membrane 170 may be defined by a microporous material including, for example, one or materials selected from a group consisting of:

Polyethylene;
Polyurethane;
Polypropylene; and,
Polytetrafluoroethylene (PTFE).

Examples of suitable vapor permeable membrane materials include various porous films such as TYVEK polyethylene films (E.I. duPont deNemours Corporation, Wilmington, Del.), GORE-TEX films (W. L. Gore and Associates, Newark, Del.), hydrophilic dense polyurethane films and porous hydrophobic polyurethane films such as those supplied by Porvair (Porvair pic., Norfolk, United Kingdom). The membrane can also have a hydrophilic coating such as SCOTCH-Guard (3M Company).

Upon depression of the actuator 112 the inner pouch is punctured so that liquid refrigerant flows from the inner pouch into the outer pouch and through the flow bands 142 into the evaporative area. In this regard, the enclosed volume of the sorption-based heat exchanger 100 may be maintained at a subatmospheric pressure, e.g., less than about 5 hectopascal (hPa) or 5 millibar (mbar), and more preferably less than about 2 hPa or 2 mbar. Further, at least a front surface 114 of the housing member 110 and an adjacent front surface 144 of the liquid refrigerant vessel 140 may both be of a flexible construction. In turn, upon actuation of the actuator 112, atmospheric pressure acting upon the front surface 114 of the housing member 110, and in turn upon the front surface 144 of the liquid refrigerant vessel 140, will facilitate the flow of liquid refrigerant through the flow bands 142 and into the evaporative area which is at a subatmospheric pressure.

By way of example, the liquid refrigerant contained in vessel 140 may comprise one or more liquids selected from a group consisting of ammonia, various alcohols such as methyl alcohol or ethyl alcohol, ketones (e.g., acetone) or aldehydes (e.g., acetaldehyde). Other useful liquids can include chlorofluorocarbons (CFC) or hydrochlorofluorocarbons (HCFC) such as FREON (E.I. Dupont de Nemours, Wilmington, Del.), a series of fluorocarbon products such as FREON C318, FREON 114, FREON 21, FREON 11, FREON 114B2, FREON 113 and FREON 112. Other useful fluorocarbons liquids include HCFC-134a, HCFC-141b and HCFC-245fa. Preferably, the liquid includes water, and in one embodiment the liquid consists essentially of water. Water is advantageous due to its high heat of vaporization, low cost and low toxicity. However, it may be desirable to include minor amounts of other components in the liquid in order to control the evaporative properties of the liquid. For example, the liquid can be mixed with a component having a low vapor pressure or with a gas, such as carbon dioxide. In one embodiment, water may be provided in vessel 140 with a volume of between about 50 ml. and 150 ml., and preferably between about 90 ml. and 110 ml.

Figure 2D:
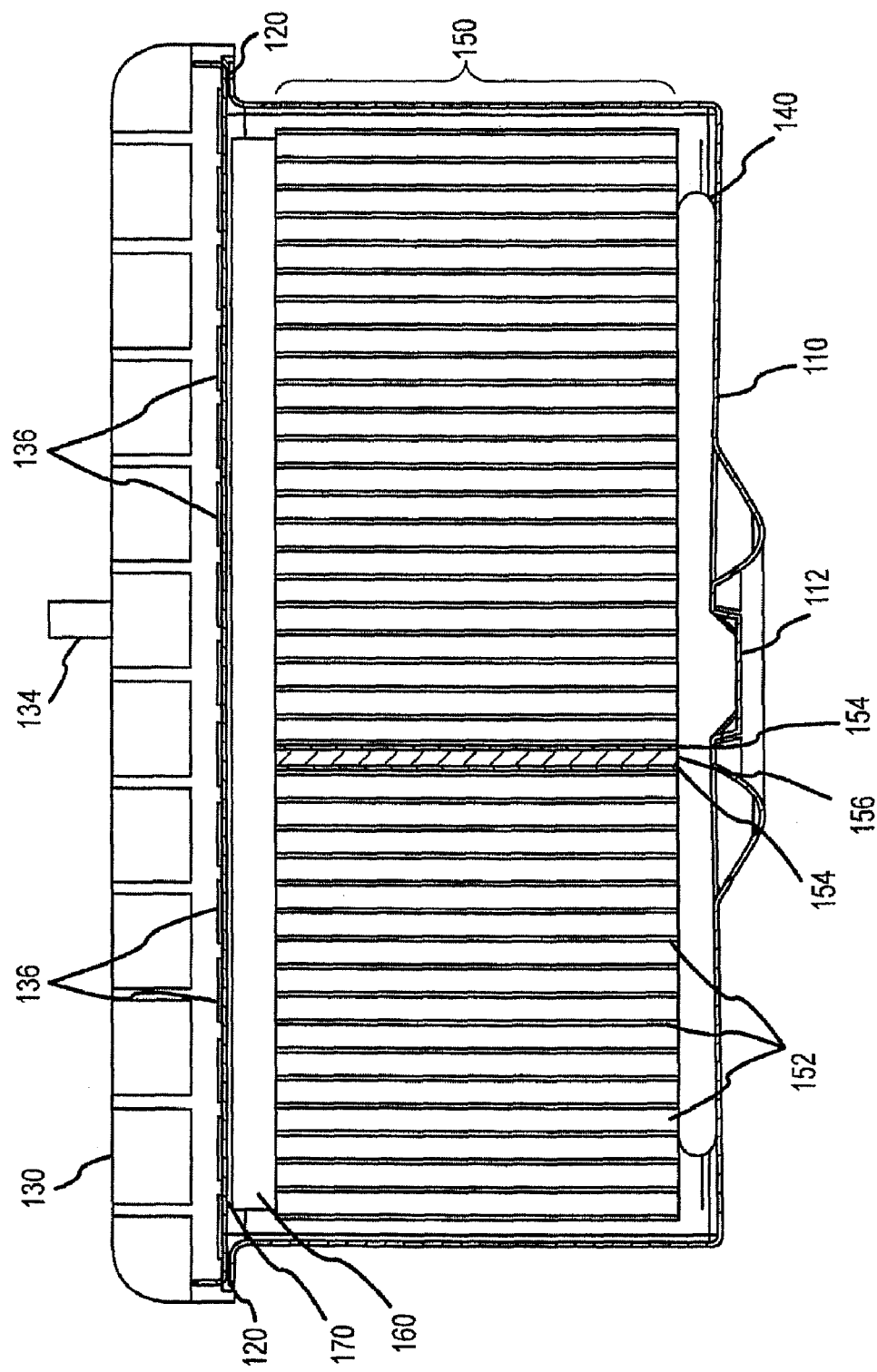
FIG. 2D illustrates a top cross-sectional view of the embodiment of FIG. 2A taken along the cut plane 2D-2D.

Reference is now made to FIG. 2D, which is a top cross-sectional view taken along cut-plane 2D-2D shown in FIG. 2C. Of note, the cooling reservoir 130 includes a plurality of fluid channels 136 that are each fluidly interconnected to inlet port 132 and fluid outlet port 134 (not shown). Such fluid interconnections will be further described in reference to FIG. 3A below. The fluid channels 136 extend along and adjacent to the back surface of the heat exchange member 120 to facilitate conductive heat transfer therebetween.

Of further note in FIG. 2D, the sorption layer 150 comprises a plurality of spacer members 152 each defining a corresponding channel region 153 therethrough for the passage of vaporized liquid refrigerant. As shown, the spacer members 152 extend perpendicularly away from the heat exchange member 120, vapor permeable membrane 170 and thermal insulation layer 160. Additionally, between each of the adjacent spacer members 152 a sorptive material 154 is provided, wherein liquid refrigerant vapor may contact and thereby be sorped by the sorptive material 154. Concomitantly, to extract thermal energy released in conjunction with such sorption, a phase change material 156 may be provided, e.g., adjacent to the sorptive material 154. In this regard, while only one spacer member set 152 is illustrated in FIG. 2 with sorptive material 154 and phase change material 156 located therebetween, it will be understood that the volume between each set of spacer members 152 may be similarly provided with sorptive material 154 and phase change material 156.

In one embodiment, the spacer members 152 may be defined by a netting material. More particularly, such netting may be an extruded material (e.g., comprising polyethylene or polypropylene) and may be of a woven nature so as to define corresponding channel regions 153. In turn, each spacer member 152 may define a corresponding channel region 153 having a thickness, or width, of between about 0.5 mm and 2 mm for vaporized liquid refrigerant passage therethrough.

In one embodiment, sorptive material 154 may comprise a desiccant material. By way of example, the desiccant material may include one or more materials selected from a group consisting of: zeolite, barium oxide, activated alumina, silica gel, glycerine, magnesium perchlorate, calcium sulfate, calcium oxide, activated carbon, calcium chloride, glycerine silica gel, alumina gel, calcium hydride, phosphoric anhydride, phosphoric acid, potassium hydroxide and sodium sulfate.

In one implementation the desiccant may be a surface modified porous material. The porous material can be a material such as activated carbon or silica. The surface modification can include impregnating the porous material with one or more metal salts such as a metal salt selected from the group consisting of calcium chloride, lithium chloride, lithium bromide, magnesium chloride, calcium nitrate, potassium fluoride and the like. The porous support material may be loaded with from about 20 to about 80 weight percent of the metal salt and more preferably from about 40 to about 60 weight percent of the metal salt. In one embodiment, a predetermined amount of sorptive material 154 may be employed to achieve a desirable amount of cooling, e.g., between about 66 gm. and 700 gm. of a desiccant, and more preferably between about 90 gm. and 300 gm. of a desiccant.

By way of example, the phase change material 156 may comprise a hydrated salt and/or a paraffin material. The phase change material may have a transition temperature of from about 10° C. to about 80° C. More preferably, the phase-change material may have a transition temperature of at least about 25° C. It is desirable to utilize phase-change materials that have a transition temperature above ambient (e.g., 25° C.) to simplify the storage of such materials. As used herein, transition temperature refers to the temperature at which the phase-change material undergoes a phase-change, e.g., from a solid to a liquid.

The phase-change material may also be provided to have a high energy density. The energy density may be measured in terms of mass (mass energy density) or volume (volumetric energy density). Mass energy density refers to the amount of energy that is released or adsorbed by the phase-change material per unit mass of the phase-change material. Volumetric energy density refers to the amount of energy that is released or adsorbed by phase-change material per unit volume of the phase-change material. The phase-change material may have a volumetric energy density of at least about 200 J/cm$^3$, more preferably at least about 275 J/cm$^3$ and most preferably at least about 350 J/cm$^3$. Exemplary phase-change materials include inorganic compounds such as disodium sulfate decahydrate, disodium hypophosphate dodecahydrate, barium hydroxide octahydrate, paraffins such as octadecane, and combinations thereof. In order to provide a range of transition temperature, it may be desirable to mix two or more phase-change materials. In one embodiment, a predetermined amount of phase change material 156 may be included to achieve a desired amount of cooling, e.g., between about 600 grams and 1600 grams, and more preferable between about 800 grams and 1200 grams. In some embodiments, it may be desirable to restrict mixing of the desiccant and the phase-change material, especially at or above the transition temperature of the phase-change material. When the phase-change material is in a liquid or gas phase, as is the case above its transition temperature, it may cause unwanted chemical reactions with the desiccant or lessen thermal communication with the desiccant by reducing the amount of phase-change material in contact with the desiccant. In such a case, a fluid diffusion barrier may be employed to prevent the phase-change material from contacting the desiccant or from changing its shape.

The fluid diffusion barrier can be any type of barrier which prevents the phase-change material from interspersing with the desiccant. The fluid diffusion barrier may also have a high thermal conductivity to enable efficient thermal communication between the desiccant and phase-change material. Exemplary fluid diffusion barriers include simple plastic films such as polyethylene, nylon, PVC, metal foils with plastic heat seal layers such as those sold by Toyo Aluminum (Osaka, Japan), metallized plastic barrier such as those sold by DuPont (Wilmington, Del.) and Rexam (London, England), multi-layer plastic layers and combinations thereof. In addition to preventing fluid diffusion, the fluid diffusion barrier may be employed to provide mechanical protection for the phase-change so that it retains its original shape and is resistant to physical or chemical changes in its structure. This may be accomplished by any means known in the art, including placement of the phase-change material in a heat-sealed pouch comprising the fluid diffusion barrier.

Figures 3A, 3B, 3C:
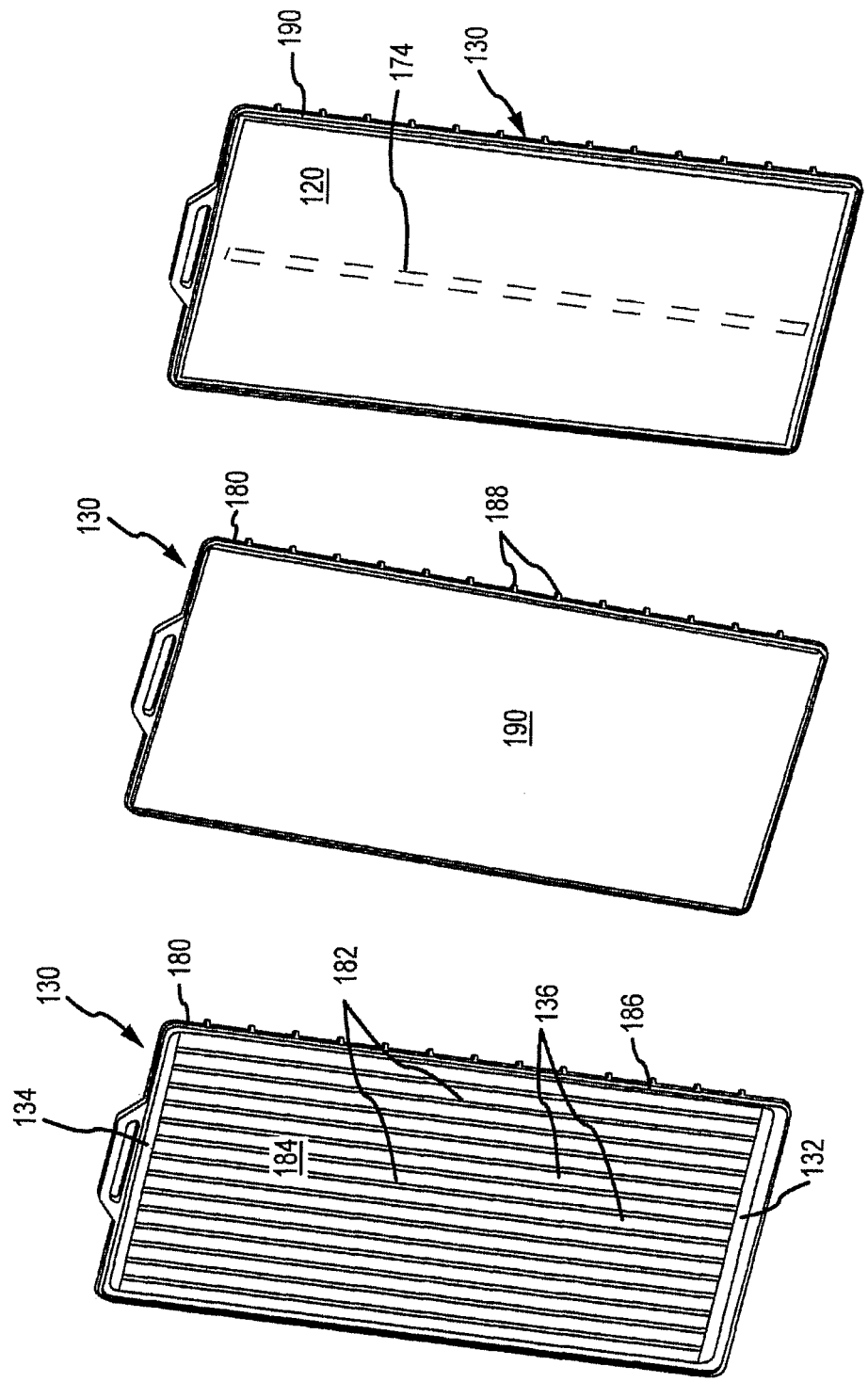
FIG. 3A illustrates a back member of the cooling reservoir of the embodiment of FIG. 2A.
FIG. 3B illustrates the back member and a front member of the cooling reservoir of the embodiment of FIG. 2A.
FIG. 3C illustrates a heat exchange member of the embodiment of FIG. 2A.

As noted above, cooling reservoir 130 of the embodiment shown in FIGS. 2A-2B may comprise a plurality of flow channels 136. In this regard, reference is now made to FIGS. 3A and 3B which illustrate a back member 180 and a front member 190 interconnected to the back member 180, respectively. In particular, and as shown in FIG. 3A, the back member 180 may include a plurality of vertically oriented ribs 182 extending away from a sheet-like layer 184 to define at least a portion of the flow channels 136 therebetween. By way of example, flow channels 136 may be provided to have a filled thickness (e.g., as measured between back member 180 and front member 190) of between about 1 mm and 0.4 mm, and preferably between about 0.15 mm and 0.25 mm. Further, the flow channels may be provided to have a length of between about 10 cm and 200 cm, and preferably between about 15 cm. and 40 cm.

In the latter regard, the internal ends of inlet port 132 and outlet port 134 extend through the layer 184 and are located so that liquid may flow through inlet port 132 into an inlet staging area adjacent to the bottom ends of the flow channels 136, through the flow channels 136, into an outlet staging area adjacent to the top ends of flow channels 136, and through outlet port 134. In one embodiment, a liquid from source reservoir(s) 20 may be passed through cooling reservoir 130 and cooled by sorption-based heat exchanger 100, wherein a liquid temperature at inlet port 132 of between about 15° C. and 30° C., and preferably between about 20° C. and 25° C. is provided, and a liquid temperature at outlet port 134 of between about 2° C. and 8° C., and preferably between about 5° C. and 7° C. is realized.

As shown in FIG. 3B, the front member 190 may be interconnected to the back member 180 about an external rim 186 and along the edges of ribs 182 of the back member 180. To provide structural support, and as shown in FIGS. 3A, 3B and 2B, the back side of the back member 180 may be provided with a plurality of transverse reinforcement members 188 (e.g., raised ribs disposed in a waffle-like pattern).

Figure 3F:
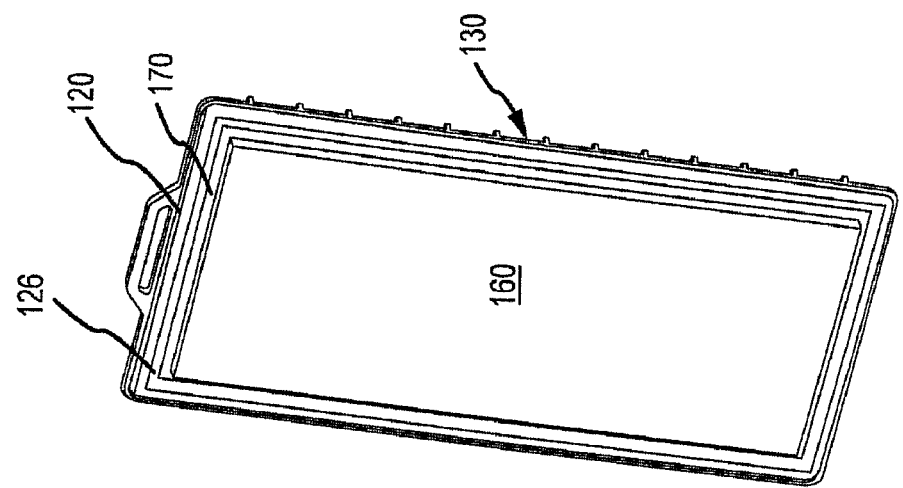
FIG. 3F illustrates a thermal insulating layer of the embodiment of FIG. 2A.

Referring now to FIG. 3C, the heat exchange member 120 of the sorption-based Heat exchanger 100 is shown in a juxtaposed position relative to a front side of the front member 190 of cooling reservoir 130. Further, an optional first distribution member 174, comprising a porous material, is shown to facilitate the distribution of a liquid refrigerant. More particularly, and with reference to both FIGS. 3C and 3D, the first distribution member 174 is positioned between the front side of the heat exchange member 120 and a back side of the vapor permeable membrane 170. In the latter regard, and as shown in FIG. 3D, the vapor permeable membrane 170 may be interconnected to a peripheral portion of the heat exchange member 120 by an open frame member 126. Further, the vapor permeable membrane 170 may be provided with a top opening 172 therethrough (e.g., located on a center axis thereof) to receive liquid refrigerant through the flow band 142 of the liquid refrigerant reservoir 140 (as shown in FIG. 2C), upon actuation of the actuator 112.

In turn, and referring again to FIG. 3C, the first distribution member 174 is located so as to have a top end thereof in adjacent relation to the opening 172 through the vapor permeable membrane 170 so that liquid refrigerant may be received at the top end of the first distribution member 174 for distribution into the evaporative area defined between the heat exchange member 120 and vapor permeable membrane 170. In this regard, the first distribution member 174 may extend along a center axis of the vapor permeable membrane 170 substantially the length of the evaporative area. Similarly, while shown in a more narrow configuration in FIG. 3C, the first distribution member 174 may be of substantially the same width as the evaporative area to further facilitate distribution of the liquid refrigerant. In one arrangement, the first distribution member 174 may comprise a wicking material, e.g., a non-woven fabric.

Figure 3E:
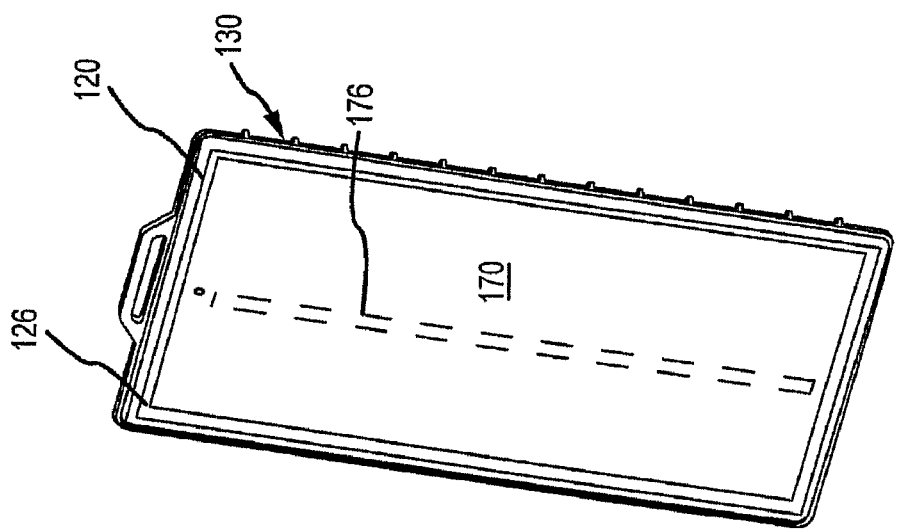
FIG. 3E illustrates an optional second distribution member of the embodiment of FIG. 2A.
Figure 3D:
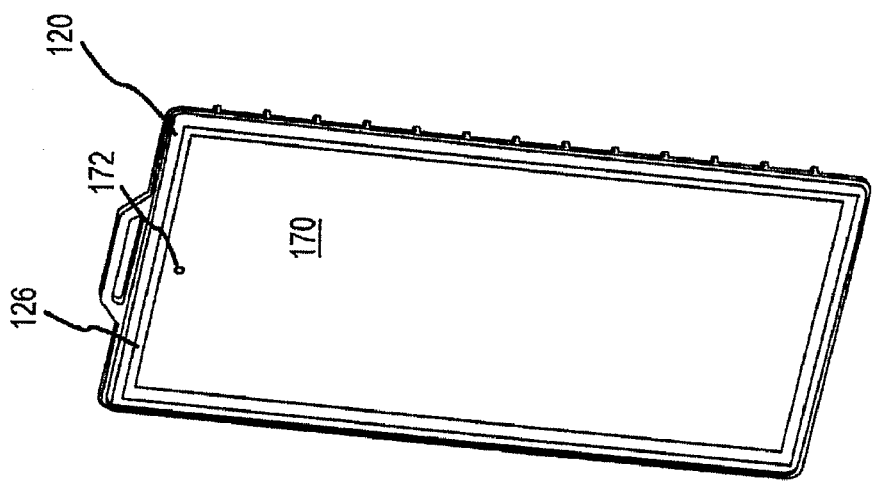
FIG. 3D illustrates a vaporpuemeable member of the embodiment of FIG. 2A.

Referring now to FIG. 3E, an optional second distribution member 176, comprising a material that is substantially impermeable to vapor, including vaporized liquid refrigerant, is illustrated for facilitating the distribution of liquid refrigerant within the evaporative area defined between the heat exchange member 120 and the vapor permeable membrane 170. More particularly, the second distribution member 176 may be interposed between a front side of vapor permeable member 170 and a back side of the thermal insulation layer 160. As shown, the second distribution member 176 may be interconnected to the front side of the vapor permeable member 170 and may be of an elongated construction extending along a center axis of the vapor permeable membrane 170. As illustrated, the optional second distribution member 176 may extend downward from a top end of and around opening 172 of the vapor permeable membrane 170. By virtue of the vapor impermeability of the second distribution member 176, the maintenance of a coincidentally-shaped open liquid refrigerant flow channel on a back side of a vapor permeable member 170 within the evaporative area may be facilitated. For example, the second distribution member 176 may yield a relatively warmer coincidental channel within the evaporative area so as to reduce any tendency for liquid refrigerant freezing along the coincidental region. In turn, the distribution of liquid refrigerant through the coincidental region may be enhanced.

Figure 3I:
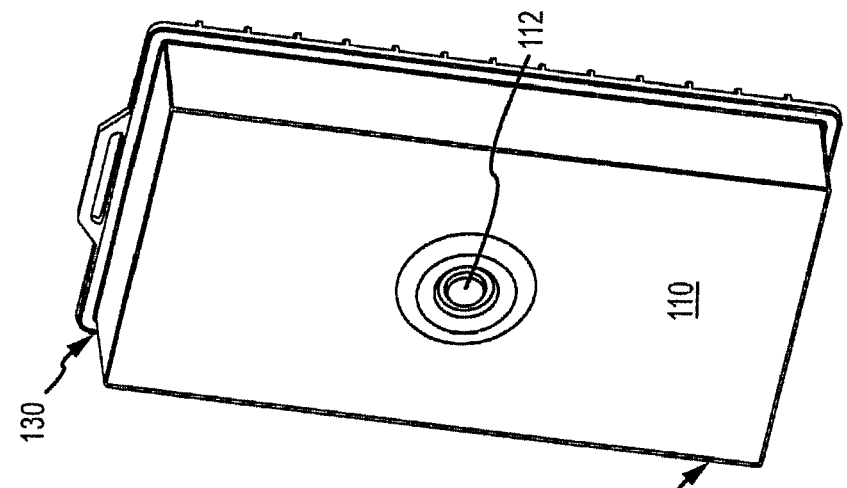
FIG. 3I illustrates an actuator of the embodiment of FIG. 2A.
Figure 3H:
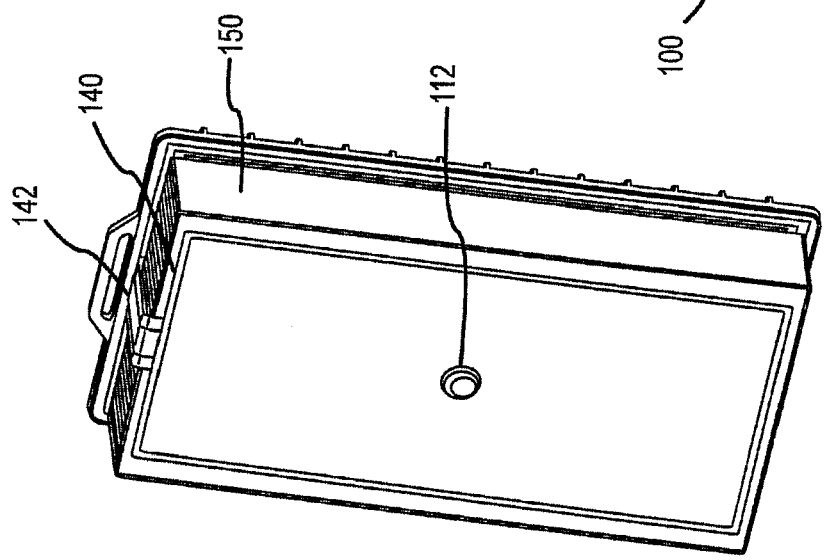
FIG. 3H illustrates a liquid refrigerant reservoir of the embodiment of FIG. 2A.
Figure 3G:
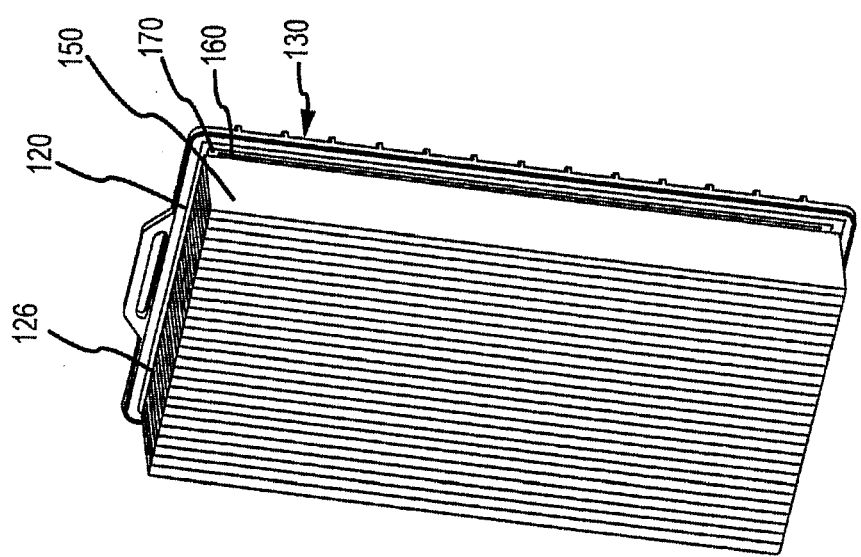
FIG. 3G illustrates a sorption layer of the embodiment of FIG. 2A.

Referring now to FIGS. 3F and 3G, thermal insulating layer 160 and the sorption layer 150 are shown in their corresponding positions, wherein respectively, the thermal insulating layer 160 is positioned adjacent to a front side of the vapor permeable membrane 170 and the sorption layer 150 is located in juxtaposed relation to a front side of the thermal insulating layer 160. In turn, FIG. 3H illustrates the liquid refrigerant reservoir 140 disposed in juxtaposed position on a front side of the sorption layer 150. As may be appreciated, the flow band 142 of the liquid refrigerant reservoir 140 may be interconnected to a front side of the vapor permeable membrane 170 at opening 172 prior to the placement and interconnection of the optional second distribution member 176, thermal insulating layer 160 and sorption layer 150. Finally, and as shown in FIG. 3I, actuator 112 may be disposed adjacent to a front side of the liquid refrigerant reservoir 140.

In one example, a portable apparatus 110 may be provided so that, prior to interconnection with an intravascular access device 90 and source(s) 20, the sorption-based heat exchanger 100 and cooling reservoir 130 have a total weight of less than about 2.5 kg, and preferably less than about 1.5 kg. Further, such embodiment may have overall dimensions of about 10"-12" (height), 4"-6" (width), and 1"-2" (thickness).

Figure 4:
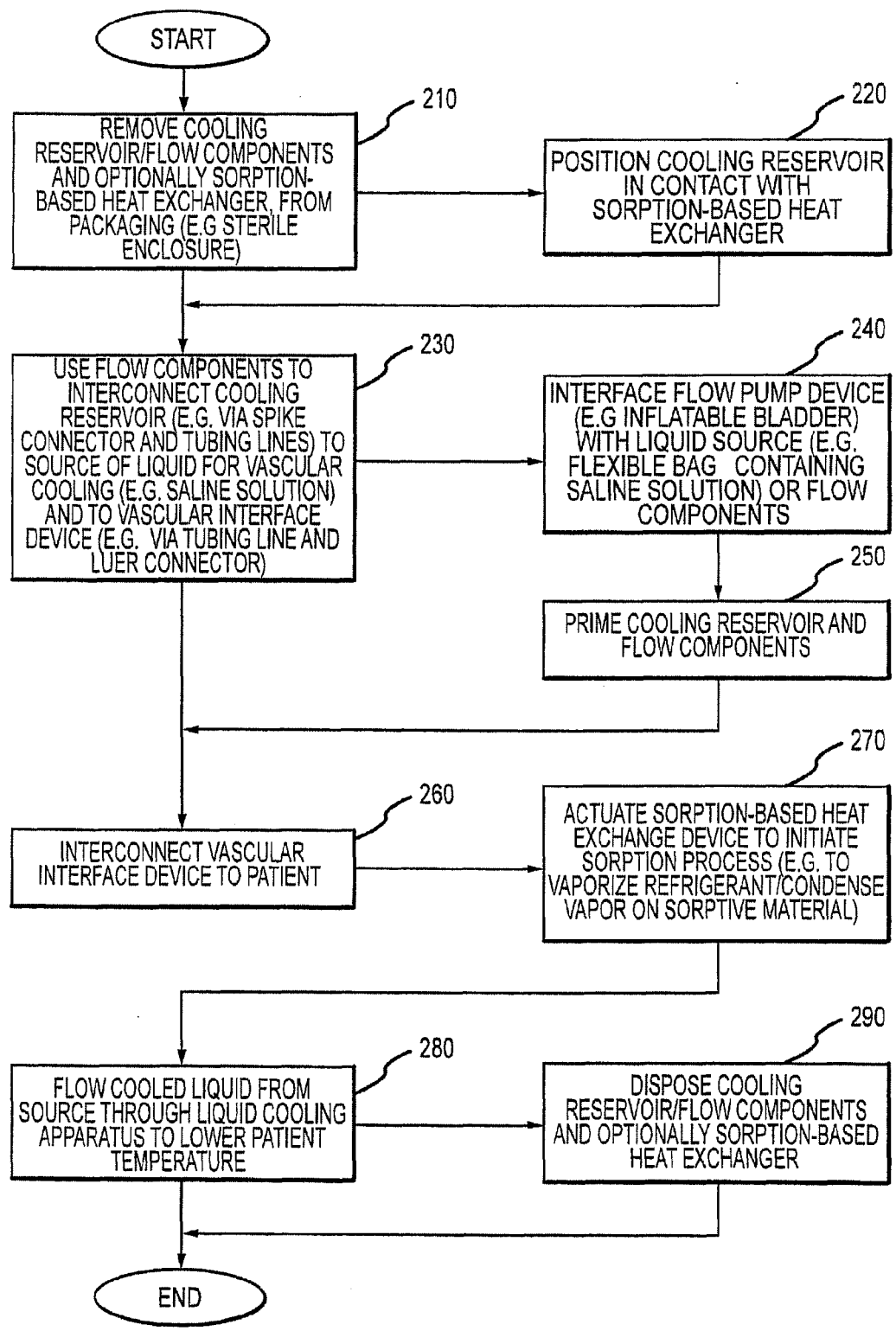
FIG. 4 illustrates one embodiment of an inventive method for providing a cooled liquid for vascular administration.

Referring now to FIG. 4, one embodiment of a method for providing cooled liquid for vascular administration will be described. In such description, various components of the above-described apparatus embodiments will be referenced to facilitate a better understanding of the methodology.

In this regard, it is contemplated that the inventive apparatus and method will provide particular advantages in the context of emergency care for patients being transported from a remote site to a patient care facility, such as a hospital. More particularly, the inventive apparatus and method are particularly adapted for use in an ambulatory vehicle where space constraints and ease-of-use are of primary importance.

In the event of an emergency procedure 200, as shown in FIG. 4, emergency personnel may initially remove a cooling reservoir 30, 130 and associated flow componentry from a sterile enclosure stored within an emergency vehicle (step 210). In this regard, such componentry may be packaged in the enclosure together at a production site, and unpackaged together at the patient care site. The associated flow componentry may include first and second liquid flow lines 60, 70, interconnected or interconnectable to the cooling reservoir 30, 130, as well as optional first and second flow control members 64, 66, optional first interconnection member 62 for first flow line 60, optional second interconnection member 72 for second flow line 70, gas removal member 74 and optional medication port 76 for second liquid flow line 70. Further, in arrangements where the cooling reservoir 30, 130 is fixedly interconnected or otherwise integrated with a sorption-based heat exchanger 50, 100, sorption-based heat exchanger 50 may also be included in the packaging noted.

In arrangements where the sorption-based heat exchanger 50 is separately provided, e.g., to facilitate reuse thereof, the cooling reservoir 30 will need to be initially positioned in contact relation to the sorption-based heat exchanger 30 after unpackaging (step 220). For example, a support slot may be provided by the sorption-based heat exchanger 50 for removably and slidably receiving the cooling reservoir 30.

Next, the various flow componentry may be utilized to interconnect the cooling reservoir 30, 130 to a source of liquid for vascular cooling 20 and to a vascular interface device 90 (step 230). For example, and in relation to the above-described embodiment 10, interconnection member 62 may be interconnected to a liquid source 20, and interconnection member 72 may be interconnected to intravascular interface device 90. Concomitantly, a flow pump device 68 may be interfaced with the liquid source 20 (step 240). By way of example, an inflatable bladder may be positioned to engage a flexible liquid source 20, wherein the inflatable bladder may be manually inflated by a user (e.g., via a hand-held pumping device) so as to apply a compressive force to the liquid source 20. After fluid interconnections have been made with the various flow componentry, such componentry may be primed with liquid from the liquid source 20 (step 250). For example, the first and/or second flow control members 64 and 66 may be moved from a first position in which liquid is restricted from flowing from liquid source 20 to a second position in which liquid may flow from the liquid source 20, through first flow line 60, cooling reservoir 30, 130 and second flow line 70.

After priming, vascular interface device 90 may be interconnected to a vascular aspect of a patient (step 260). By way of example, an IV catheter may be inserted into a patient's vascular system in a conventional manner.

To initiate patient cooling, adsorption-based heat exchanger 50, 100, may then be actuated, via depression of actuator 112 of heat exchanger 130, so as to cool liquid passing into cooling reservoir 30, 130 (step 270). As previously discussed, in relation to sorption-based heat exchanger 100, such actuation will result in the flow of liquid refrigerant from refrigerant vessel 140 into an evaporative area of sorption-based heat exchanger 100, whereupon the refrigerant vaporizes and thermal energy is conducted from the liquid in the cooling reservoir 30, 130. In turn, the cooled liquid is flowed into the vascular system of the patient via the second flow line 60, via interconnection member 72 and vascular interface device 90. As may be appreciated, the flow and cooling of liquid from source 20 may continue until the patient has been cooled to a desired temperature and/or otherwise reaches the hospital or other care facility.

When vascular cooling of the patient is completed, the various flow components, cooling reservoir 30, 130 and utilized liquid source(s) 20 may be disposed of. Again, when the sorption-based heat exchanger 30, 130 is fixedly interconnected or otherwise integrated with a cooling reservoir 30, 130, such sorption-based heat exchanger 30, 130 may be disposed together with the above-noted items.

Figure 5:
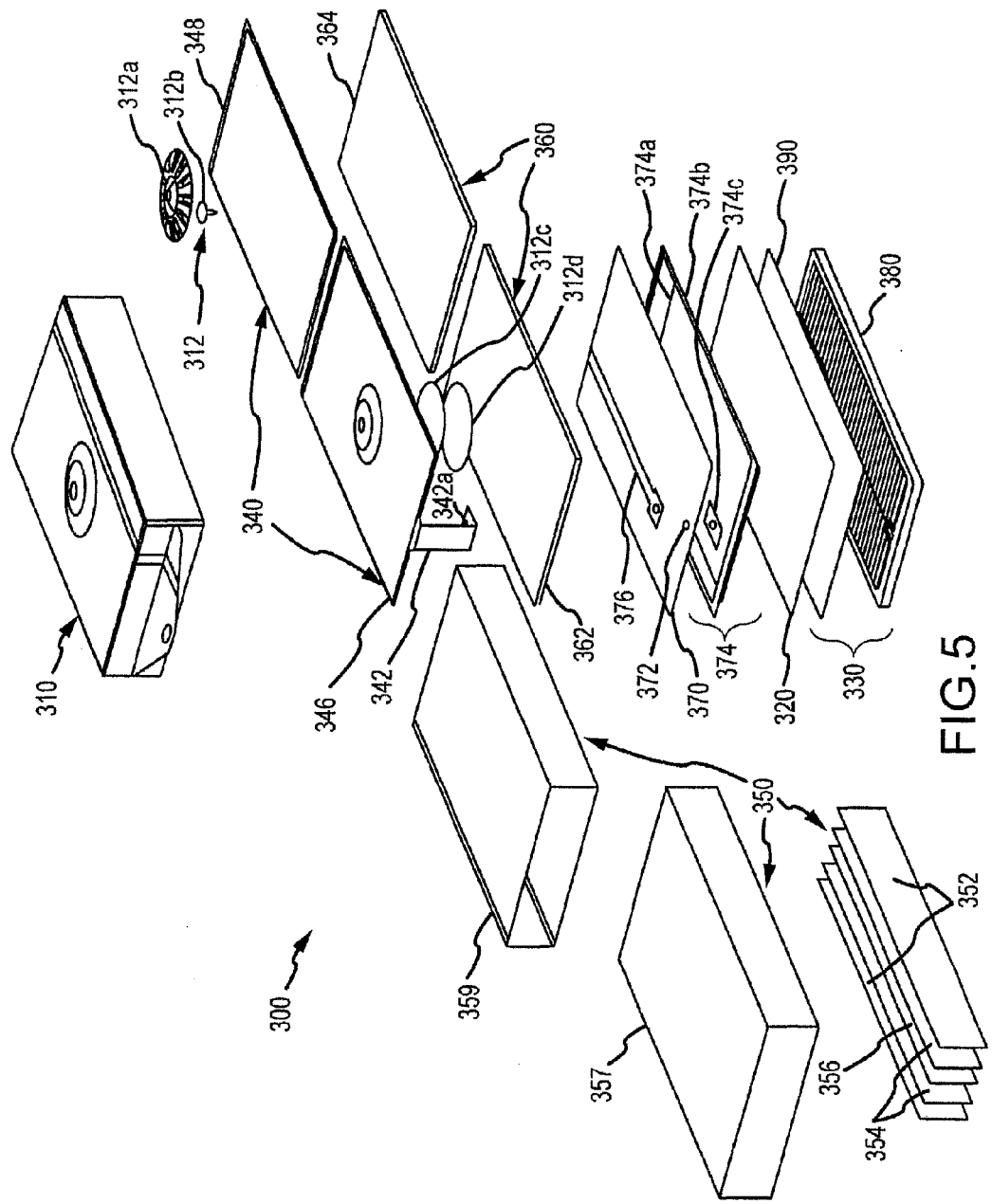
FIG. 5 illustrates an exploded assembly view of another embodiment of a sorption-based heat exchanger and adjacently-disposed cooling reservoir comprising the present invention.

FIGS. 5, 6A-6C, 7 and 8 illustrate another embodiment of a sorption-based heat exchanger 300 and cooling reservoir 330 that comprise components and are operable in a manner similar to that of the sorption-based heat exchanger 100 and cooling reservoir 130 described above, respectively. In general, the cooling reservoir 330 may be defined by a back member 380 and a front member 390. In turn, the sorption-based heat exchanger 300 includes, a heat exchange member 320, interconnected to a front side of the cooling reservoir 330, and a housing member 310 interconnected to a front side of the heat exchange member 320 to define an enclosed volume therebetween that may house additional components of the sorption-based heat exchanger 300 in a layered manner. FIG. 5 illustrates such additional componentry, wherein "front" and "back" sides of the components are facing upwards and downwards, respectively, and wherein top ends and bottom ends of the components are located on the left and right sides, respectively.

As shown in FIG. 5, an optional first distribution member 374 may be located adjacent to a front side of the heat exchange member 320, a vapor permeable membrane 370 may be located adjacent to a front side of the heat exchange member 320 and first distribution member 374, an optional second distribution member 376 may be located adjacent to a front side of the vapor permeable membrane 370, a thermal insulating layer 360 may be located adjacent to a front side of the vapor permeable membrane 370 and second distribution member 376, a sorption layer 350 may be located adjacent to a front side of the thermal insulating layer 360 and a liquid refrigerant vessel 340 may be located adjacent to a front side of the sorption layers 150. The heat exchange member 320, vapor permeable membrane 370, sorption layer 350 and liquid refrigerant vessel 340 may be of a construction analogous to the heat exchange member 120, vapor permeable membrane 170, sorption layer 150, and liquid refrigerant vessel 140, respectively, described above in relation to the sorption-based heat exchanger 100.

The first distribution member 374 may comprise a porous wicking material 374b (e.g., a non-woven fabric material) held in position relative to heat exchange member 320 by an outer adhesive frame member 374b. In the latter regard, the frame member 374b may comprise adhesive on both a front side and back side thereof, wherein the wicking member 374 is held in position between the frame member 374b and heat exchange member 320, and wherein the vapor permeable membrane 370 is held in position by and relative to the adhesive front surface of the frame member 374b. Optionally, a double-sided adhesive locator 374c may be interconnected to a front side of the wicking member 374a and to a bottom side of the vapor permeable membrane 370, wherein an opening through the locator 374c is aligned with an opening 372 through a top end of the vapor permeable membrane 370. In this regard, in operation liquid refrigerant may pass from the liquid refrigerant vessel 340 through a flow band 342 thereof through the opening 372 of the vapor permeable membrane 370, and through the corresponding opening through the locator 374c, wherein the liquid refrigerant may then be distributed by the first distribution member 374 within an evaporative area defined between the heat exchange member 320 and vapor permeable membrane 370.

The second distribution member 376 may comprise a vapor impermeable material having an adhesive surface disposed on at least a back side thereof for connection to the vapor permeable membrane 370. In one approach, a pressure-sensitive acrylic adhesive transfer tape may be employed, wherein a first adhesive side may be applied to the vapor permeable membrane 370 and a polycoated kraft liner removed from a second adhesive side thereof (e.g., product reference 468MP offered by 3M Company of St. Paul, Minn.). The second distribution member 376 may include an opening disposed in aligned relation with the opening 370 of the vapor permeable membrane 370. In turn, the flow band 342 of the liquid refrigerant vessel 340 may be adhesively interconnected to a top end of the second distribution member 376, wherein a fluid outlet 342a of the flow band 342 is disposed in aligned relation with the openings of the second distribution member 376, the vapor permeable membrane 370 and the locator 374c. The optional second distribution member 376 may be utilized to reduce any tending for freezing on a back side of the vapor permeable membrane 370, thereby facilitating the distribution of liquid refrigerant that flows into the evaporative area between a front side of the heat exchange member 320 and a back side of the vapor permeable membrane 370 during use.

As shown in FIG. 5, the thermal insulating layer 360 may be defined by a porous insulation member 362 disposed within a porous, outer envelope 364. By way of example, the insulating member 362 may be defined by a plurality of netting material layers (e.g., comprising extruded polyethylene or polypropylene), while the envelope 364 may be defined by a non-woven fabric material (e.g., a 40 gram per square meter, spunbonded polypropylene fabric) having relatively non-abrasive outer surfaces to reduce undesired interference between the insulating layer 360 and the vapor permeable membrane 370 as well as other interfacing components.

In the latter regard and as shown in FIG. 5, the sorption layer 350 may be located adjacent to a front surface of the envelope 364 of the insulating layer 360 and adjacent to a back surface of the liquid refrigerant vessel 340, wherein the flow band 342 of the liquid refrigerant vessel 340 may wrap around a top end of the sorption layer 350. With particular reference to the sorption layer 350, a plurality of sets of spacer members 352, sorption material layers 354 and phase-change material layers 356 may be arranged in a stack, or bundle 357, wherein the bundle 357 may be held in compressive, interfaced engagement via an outer porous retaining member 359 (e.g., a fabric material wrapped tightly about and heat-sealed along edges to maintain compression of the stack 357). By way of example, a single set is shown in FIG. 5, wherein each set may include a pair of spacer members 352, with an adjacent pair of sorption material layers 354 and a single layer of a phase-change material 356 located therebetween in a laminated fashion.

With further reference to FIG. 5, the liquid refrigerant vessel 340 may comprise an outer sealed pouch 346 of flexible construction and an inner sealed pouch 348 disposed within the outer pouch 346. The inner pouch 348 may comprise a predetermined volume of liquid refrigerant (e.g., a water-based refrigerant as described above) which may be selectively passed from within the inner pouch 348 into the outer pouch 346 for passage via flow band 342 into the evaporative area defined between the vapor permeable membrane 370 and heat exchange member 320 described hereinabove. The inner pouch 348 may be fluid-tight and restrict the passage of vapor and gas therethrough. For example, the inner pouch 348 may be of a multilaminate construction including a first vessel that comprises a fluid diffusion barrier material (e.g., a metal foil), and a second vessel comprising a reinforcement material (e.g., a polymer-based material). In one arrangement, two reinforcement layers are utilized, one comprising polyethylene and another comprising polyester).

As shown, an actuator 312 may be provided for selectively penetrating the inner pouch 348 of the liquid refrigerant vessel 340 to permit passage of the liquid refrigerant from the inner pouch 348. In this regard, the actuator 312 may include a dome member 312a and an underlying actuator tack 312b both positioned inside and adjacent to the front of the outer pouch 346 and outside and adjacent to the front of the inner pouch 348 of the liquid refrigerant vessel 340. Further, a support member 312c and an underlying anvil member 312d, corresponding in shape with the dome member 312a, may be located inside and adjacent to the back of the outer pouch 346 and outside and adjacent to the back of the inner pouch 346.

As illustrated, a top layer of the outer pouch 346 of the liquid refrigerant reservoir 340 and a top layer of the outer housing 310 may be configured in a coincidental configuration relative to the dome member 312d to facilitate positioning and operation of the actuator 312.

The outer housing 310, may be fluid-tight and restrict the passage of vapor and gas therethrough. For example, the outer housing 310 may be of a multilaminate construction including a first vessel that comprises a fluid diffusion barrier material (e.g., a metal foil), and a second vessel comprising a reinforcement material (e.g., a polymer-based material). In one arrangement, two reinforcement layers are utilized, one comprising polyethylene and another comprising polyester.

Figure 6A:
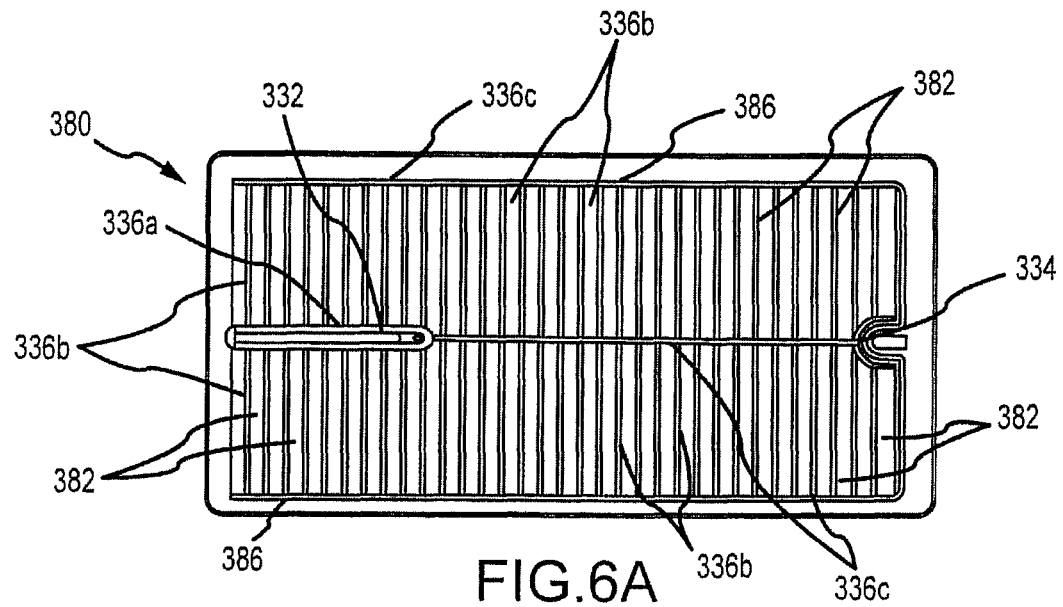
FIGS. 6A, 6B and 6C illustrate a front view, back view and side view of a back member of a cooling reservoir of the embodiment of FIG. 5.
Figure 6B:
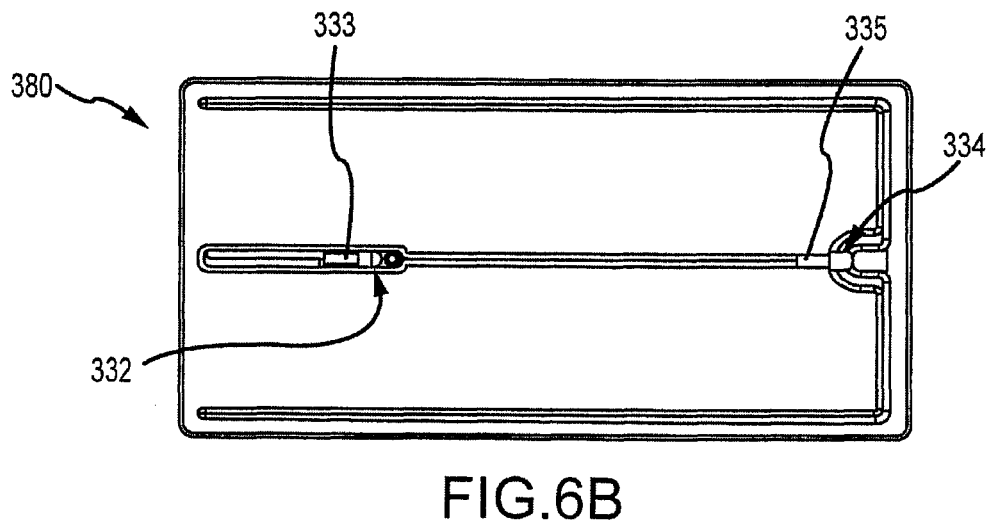
Figure 6C:
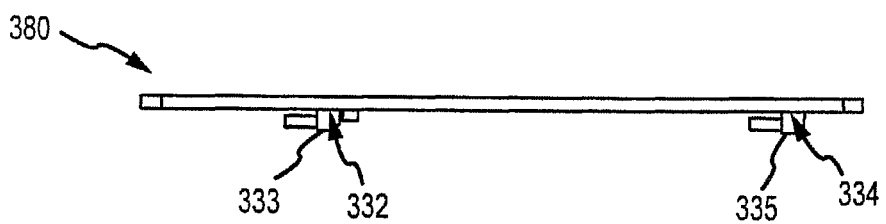

Referring now to FIGS. 6A, 6B and 6C, the back member 380 of cooling reservoir 330 will be further described. As shown in FIG. 6A, the back member 380 may include an inlet port 332 and outlet port 334 through which liquid may be passed for cooling within the cooling reservoir 330 and provided to a patient for vascular administration as described hereinabove. More particularly, an inlet channel 336a may be located adjacent to the inlet port 332 for distributing liquid from the inlet port 332 to a bottom end of the cooling reservoir, illustrated at the left side of FIGS. 6A, 6B and 6C. In turn, the outwardly extending lateral channels 336b adjoin the distribution channel 336a, wherein liquid may pass through the lateral channels 336b. Further, interconnected longitudinal channels 336c may be provided along a center axis and the outside periphery of the back member 380. As illustrated, lateral channels 336b may be interconnected to the longitudinal channels 336c along the length of the back member 380 to facilitate the flow of liquid through the cooling reservoir 330 to outlet port 334. The various channels described above may be defined above by raised ribs 382 and peripheral ribs 386.

As shown in FIGS. 6B and 6C, the inlet port 332 and outlet port 334 of the back member 380 may be provided with interconnected L-shaped, or elbow members 333 and 335, respectively, to facilitate interconnections and routing of liquid flow lines as well as compact packaging. By way of example, the L-shaped members 333, 335 may be integrally formed with the back member 380 (e.g. molded polyethylene).

Figure 7:
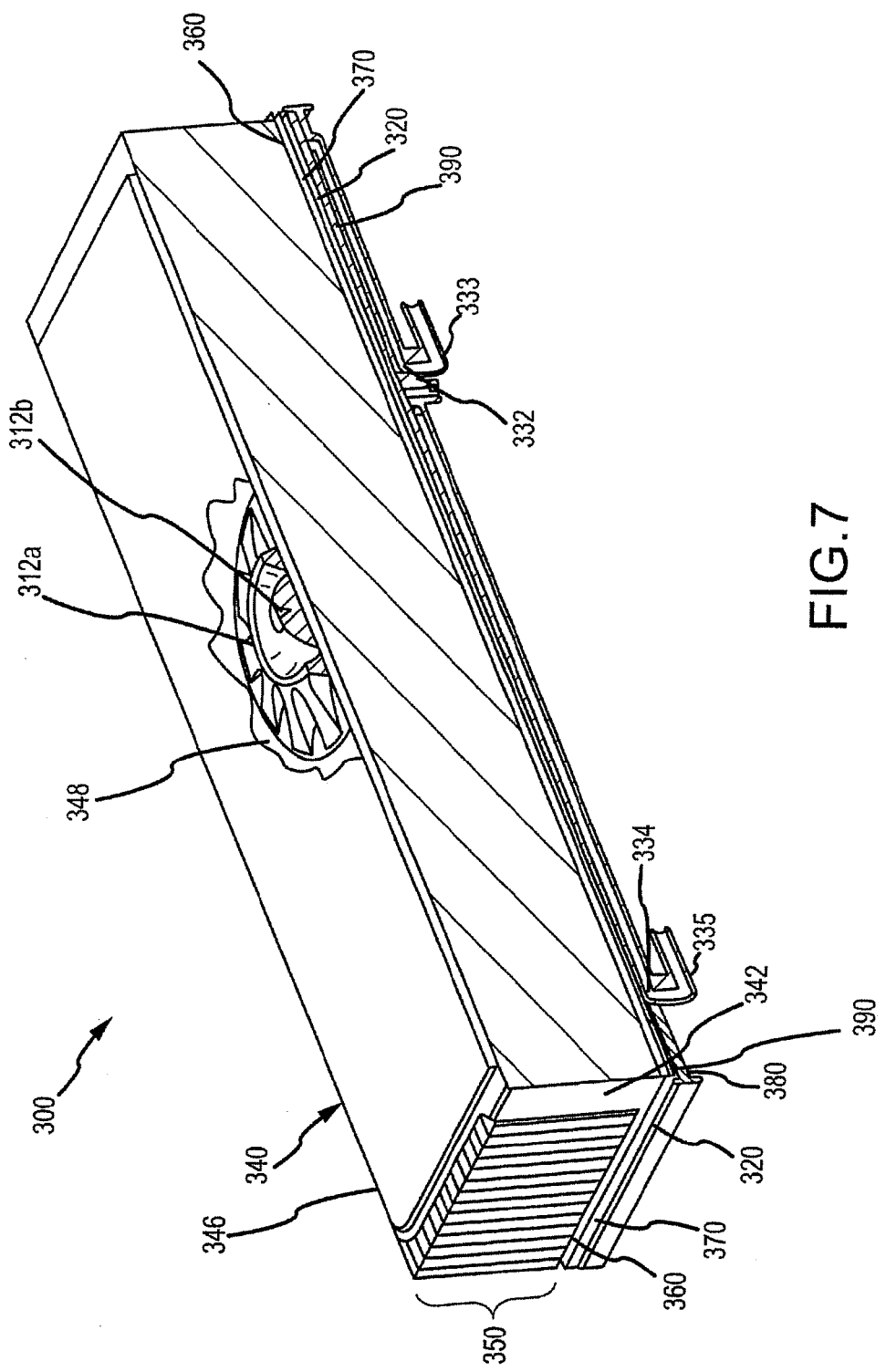
FIG. 7 illustrates a perspective cross-sectional view of the embodiment of FIG. 5, with a housing member removed and a portion of an outer pouch of a liquid refrigerant cooling reservoir cut away.

Reference is now made to FIG. 7 which illustrates a cross-sectional view of the sorption-based heat exchanger 300 with the outer housing 310 removed for purposes of illustration. As shown, the actuator dome 312a is configured to define a cup-shaped, middle dome portion and an inverted U-shaped annular portion thereabout. Such a configuration facilitates plastic deformation of the actuator dome 312a upon the application of force upon the middle dome portion, wherein the actuator dome 312a may be plastically deformed from a first set position, shown in FIG. 7, to a second set position in which the actuator tack 312b has penetrated the inner pouch 348. In this regard, actuator tack 312b may be located on a center axis of the middle dome portion of the dome member 312a, wherein upon the application of force to the middle dome portion (e.g., manually by a user's finger) the dome member 312a will plastically deform inward forcing the actuator tack 312b inward so as to penetrate through the inner pouch 348 of the liquid refrigerant vessel 340. The actuator tack 312b may penetrate through both sides of the inner pouch 348 and be stopped from penetration of outer pouch 346 upon contacting the anvil 312d. The support member 312c may comprise an extruded netting material (e.g., a 0.01" thick disc of polyester) so as to support the inner pouch 348 and allow the actuator tack 312b to penetrate completely through both sides of the inner pouch 348. Upon penetration of the inner pouch 348, liquid refrigerant contained within the inner pouch 348 may pass into the outer pouch 346, through the flow band 342 and into the evaporative area defined between the heat exchanger 320 and vapor permeable membrane 310, wherein vaporization and attendant cooling may occur.

Figure 8:
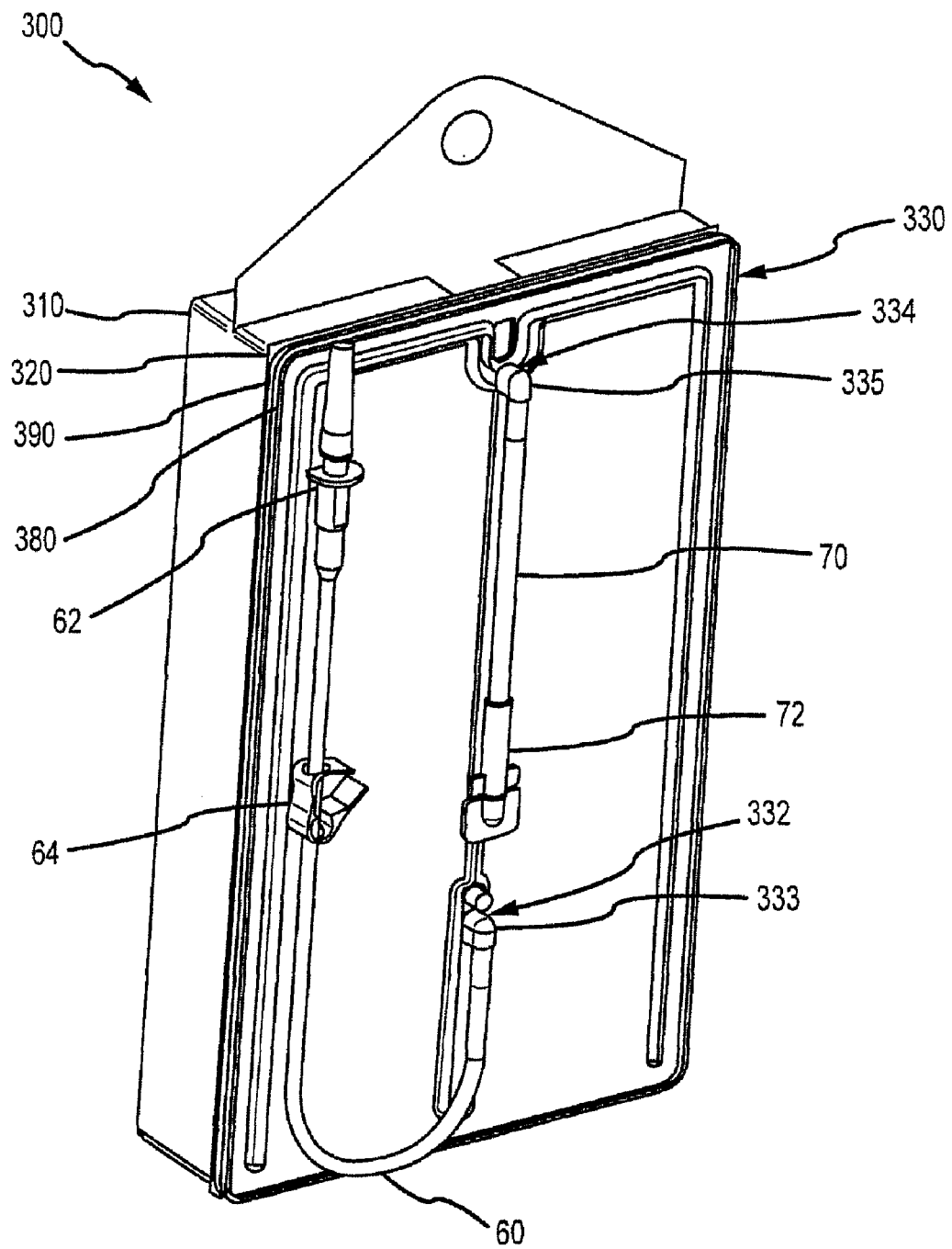
FIG. 8 illustrates a perspective rear view of a cooling reservoir of the embodiment of FIG. 5.

Reference is now made to FIG. 8 which shows the back surface of the back member 380 of the cooling reservoir 330. More particularly, FIG. 8 illustrates various flow componentry that may be interconnected to and packaged together with the cooling reservoir 330. In particular, a first liquid flow line 60 (e.g., a flexible tubing line) may be fluidly interconnected at a first end to the inlet port 332 via L-shaped member 333. Further, the first liquid flow line 60 may selectively be interconnectable at a second end to a source reservoir(s) 20 (as shown in FIG. 1) containing a liquid appropriate for cooling a patient via vascular administration. In this regard, at least one interconnection member 62 (e.g., a bag spike with a vented cap) may be provided at the second end of the first liquid flow line 60. Additionally, a first control member 64 may be included for controlling the flow of liquid through the first liquid flow line 60. By way of example, the flow control member 64 may comprise a V-shaped clamp member that depressively engages, and thereby occludes, a portion of a flexible first liquid flow line 60.

With further reference to FIG. 8, a second liquid flow line 70 (e.g., a flexible tubing line) may be interconnected to the outlet port 334 of the sorption-based heat exchanger 330 via L-shaped member 335. In turn, a second end of the second liquid flow line 70 may be fluidly interconnectable to an intravascular device 90 as previously described. In this regard, an interconnection member 72 may be provided at the second end of the second liquid flow line 70. By way of example, the interconnection member 72 may take the form of a twist-off spikeable port (e.g., having a non-resealable septum accessible upon twist-off removal of an end piece having two opposing flanges in a butterfly configuration).

The above-noted embodiments are for the purpose of illustration and are not intended to limit the scope of the present invention or patent. Rather, various modifications, adaptations and extensions of the invention will be apparent to those skilled in the art and are intended to be within the scope of the present invention as contemplated by the claims that follow.

What is claimed is:

1. A portable apparatus for selective, on-demand bodily cooling of a patient by providing a cooled liquid for administration into a vascular system of a patient, comprising:
a portable source of a liquid for vascular administration;
a portable cooling reservoir for receiving liquid from said source, including:
an inlet that is one of interconnected and interconnectable to the portable source for receiving said liquid therefrom;
an outlet that is one of interconnected and interconnectable to a vascular interface device;
a portable sorption-based heat exchanger for cooling said liquid received in said portable cooling reservoir from said portable source, free from electrical power requirements, including:
a vessel containing refrigerant;
an evaporative area for receiving and vaporizing said refrigerant therein;
a sorptive material for sorping vaporized refrigerant; and,
a heat exchange member for conducting thermal energy from said liquid received in said portable cooling reservoir into said evaporative area; and,
an actuator selectively actuable by a user to flow said refrigerant from said vessel into said evaporative area to provide selective cooling of said liquid received in said portable cooling reservoir for vascular administration to a patient.

2. A portable apparatus as recited in claim 1, wherein said cooling reservoir comprises:
at least one flow channel for flowing said liquid between said inlet and said outlet.

3. A portable apparatus as recited in claim 2, wherein said cooling reservoir further comprises:
a plurality of flow channels for flowing said liquid between said inlet and said outlet.

4. A portable apparatus as recited in claim 3, wherein at least a portion of each of said plurality of flow channels extends adjacent to said heat exchange member for thermal conduction therebetween.

5. A portable apparatus as recited in claim 4, wherein said at least a portion of each of said plurality of flow channels extends substantially parallel to a corresponding surface portion of said heat exchange member.

6. A portable apparatus as recited in claim 2, wherein said at least one flow channel follows a non-linear path between said inlet and said outlet of said cooling reservoir.

7. A portable apparatus as recited in claim 2, wherein said inlet of said reservoir is operatively located above said outlet of said cooling reservoir.

8. A portable apparatus as recited in claim 1, wherein said cooling reservoir is removably positionable adjacent to said heat exchange member of said sorption-based heat exchanger.

9. A portable apparatus as recited in claim 1, wherein said cooling reservoir is fixedly positioned adjacent to said heat exchange member of said sorption-based heat exchanger.

10. A portable apparatus as recited in claim 1, wherein said cooling reservoir is one of removably positionable and fixedly positioned in direct contact with a first side of said heat exchange member of said sorption-based heat exchanger, and wherein said evaporative area and sorptive material are located on an opposing second side of said heat exchange member of the sorption-based heat exchanger.

11. A portable apparatus as recited in claim 10, wherein said evaporative area and said sorptive material are located within an enclosed volume having a predetermined subatmospheric pressure.

12. A portable apparatus as recited in claim 11, wherein said predetermined subatmospheric pressure is between about 0.5 hPa and 4 hPa.

13. A portable apparatus as recited in claim 11, wherein said actuator is selectively actuatable to flow said refrigerant from said vessel into said enclosed volume.

14. A portable apparatus as recited in claim 13, wherein said vessel is at least partially defined by a flexible surface exposed to atmospheric pressure, and wherein upon selective actuation of said actuator a flow path is defined between said vessel and said enclosed volume.

15. A portable apparatus as recited in claim 13, wherein said sorption-based heat exchanger further comprises:
   a vapor permeable membrane disposed between said evaporative area and said sorptive material within said enclosed volume.

16. A portable apparatus as recited in claim 15, wherein said sorption-based heat exchanger further comprises:
   at least one spacer member extending through said sorptive material to define at least one corresponding channel for receiving vaporized refrigerant therethrough.

17. A portable apparatus as recited in claim 15, wherein said sorption-based heat exchanger further comprises:
   a thermal insulation layer disposed between said membrane and said sorptive material.

18. A portable apparatus as recited in claim 13, wherein said sorption based heat exchanger further comprises:
   a phase change material for extracting thermal energy, wherein said at least a portion of said phase change material is located adjacent to at least a portion of said sorptive material.

19. A portable apparatus as recited in claim 13, further comprising an envelope member interconnected to said heat exchanger member to define said enclosed volume therebetween.

20. A portable apparatus as recited in claim 13, wherein at least a portion of said actuator extends through said envelope for selective contact by a user.

21. A portable apparatus as recited in claim 1, further comprising:
   a flow pump device for maintaining the flow of said liquid from said source to said reservoir above a predetermined rate.

22. A portable apparatus as recited in claim 21, wherein said flow pump device is operable to flow said liquid into and out of said reservoir at a predetermined rate of between about 20 ml./min. and 200 ml./min.

23. A portable apparatus as recited in claim 21, wherein said flow pump device is non-electrical.

24. A portable apparatus as recited in claim 23, wherein said flow pump device comprises:
   an inflatable bladder positionable to apply a compressive force to said source of liquid.

25. A portable apparatus as recited in claim 23, wherein said flow pump device is hand-actuatable.

26. A portable apparatus as recited in claim 1, wherein said apparatus is operable to cool liquid received in said reservoir by between about 7° C. and 26° C.

27. A portable apparatus as recited in claim 26, wherein said reservoir defines an internal volume of between about 33 ml. and 134 ml.

28. A portable apparatus as recited in claim 27, wherein said reservoir and said heat exchange member directly contact each other across an area of between about 400 cm$^2$ and 1,200 cm$^2$.

29. A portable apparatus as recited in claim 26, wherein said liquid source comprises between about 1 liter and 3 liters of said liquid.

30. A portable apparatus as recited in claim 26, wherein said sorption-based heat exchanger includes between about 90 gms. and 300 gms. of said sorptive material.

31. A portable apparatus as recited in claim 26, wherein said apparatus is operable to flow liquid into and out of said cooling reservoir to provide a total energy transfer of between about 14.5 kcal and 60 kcal.

32. A portable apparatus as recited in claim 1, wherein said source of liquid comprises at least one source reservoir.

33. A portable apparatus as recited in claim 32, wherein said at least one source reservoir and said cooling reservoir are one of fluidly interconnected and fluidly interconnectable by at least one liquid flow line.

34. A portable apparatus as recited in claim 33, wherein said at least one liquid flow line is selectively fluidly interconnectable to said at least one source reservoir by at least one interconnection member.

35. A portable apparatus as recited in claim 34, wherein said at least one interconnection member comprises one of a spike and a luer connector.

36. A portable apparatus as recited in claim 32, wherein said liquid is flowable out of and not in to said at least one source reservoir.

37. A portable apparatus as recited in claim 32, wherein said cooling reservoir is adapted to be selectively fluidly interconnected to a patient by at least one liquid flow line.

38. A portable apparatus as recited in claim 37, wherein said at least one liquid flow line is selectively fluidly interconnectable to the vascular system of said patient by at least one intravascular access device.

39. A portable apparatus as recited in claim 38, wherein said at least one intravascular access device comprises a vascular catheter for passing said cooled liquid to flow into the vascular system of a patient.

40. A portable apparatus as recited in claim 32, wherein said at least one source reservoir is removably positionable relative to said cooling reservoir.

41. A portable apparatus for selective, on-demand bodily cooling of a patient by providing a cooled liquid for administration into a vascular system of a patient, comprising:
   a portable source of a liquid for vascular administration;
   a portable cooling reservoir for receiving liquid from said source, including:
      an inlet that is one of interconnected and interconnectable to the portable source for receiving said liquid therefrom; and
      an outlet that is one of interconnected and interconnectable to a vascular interface device, wherein said cooling reservoir defines a sterile internal volume for receiving and cooling said liquid from said source;
   a sterile first liquid flow line being one of fluidly interconnected and fluidly interconnectable between said source and said cooling reservoir;
   a sterile second liquid flow line being one of fluidly interconnected and fluidly interconnectable between said cooling reservoir and a vascular interface device;
   a portable sorption-based heat exchanger for cooling said liquid received in said portable cooling reservoir from said portable source, free from electrical power requirements, including:
      a vessel containing refrigerant;
      an evaporative area for receiving and vaporizing said refrigerant therein;
      a sorptive material for sorping vaporized refrigerant; and, a heat exchange member for conducting thermal energy from said liquid received in said portable cooling reservoir into said evaporative area; and, an actuator selectively actuable by a user to flow said refrigerant from said vessel into said evaporative area to provide selective cooling of said liquid received in said portable cooling reservoir for vascular administration to a patient.

42. A portable apparatus as recited in claim 41, further comprising:

an enclosure containing, in a sterile, enclosed area, at least said cooling reservoir, said first liquid flow line and said second liquid flow line prior to use.

43. A portable apparatus as recited in claim 42, wherein said enclosure further contains, in said sterile enclosing area, said sorption-based heat exchanger prior to use.

44. A portable apparatus as recited in claim 43, further comprising:

at least one flow control member disposed along and in contact engagement with said first liquid flow line for controlling the flow of liquid therethrough, wherein said at least one flow control member is contained in said sterile enclosed area of said enclosure prior to use.

45. A portable apparatus as recited in claim 42, further comprising:

an interconnection member being one of interconnected and interconnectable to one end of said first liquid flow line and adapted for selective fluid interconnection to said source of liquid for vascular administration, wherein said interconnection member is contained in said sterile enclosed area of said enclosure prior to use.

46. A portable apparatus as recited in claim 42, further comprising:

a gas removal device disposed in-line with said second liquid flow line for removing gas from liquid flowing therethrough, wherein said gas removal device is contained in said sterile enclosed area of said enclosure prior to use.

47. A portable apparatus as recited in claim 42, further comprising:

at least one interconnection member being one of interconnected and interconnectable to one end of said second liquid flow line for selective fluid interconnection to a vascular access device, wherein said interconnection member is contained in said sterile enclosed area of said enclosure prior to use.

48. A portable apparatus as recited in claim 47, wherein said at least one interconnection member comprises a luer connector.

49. A portable apparatus for selective, on-demand bodily cooling of a patient by providing a cooled liquid for administration into a vascular system of a patient, comprising:

a portable source of a liquid for vascular administration;

a portable cooling reservoir for receiving liquid from said source, including:

an inlet that is one of interconnected and interconnectable to the portable source for receiving said liquid therefrom; and an outlet that is one of interconnected and interconnectable to a vascular interface device;

a portable sorption-based heat exchanger for cooling said liquid received in said portable cooling reservoir from said portable source, free from electrical power requirements, including:

a vessel containing refrigerant;

an evaporative area for receiving and vaporizing said refrigerant therein;

a sorptive material for sorping vaporized refrigerant; and, a heat exchange member for conducting thermal energy from said liquid received in said portable cooling reservoir into said evaporative area; and, an actuator selectively actuable by a user to flow said refrigerant from said vessel into said evaporative area to provide selective cooling of said liquid received in said portable cooling reservoir for vascular administration to a patient;

wherein said apparatus is operable to cool liquid received in said reservoir by between about 7° C. and 26° C., and wherein said apparatus is operable to flow said liquid from said liquid source into and out of said cooling reservoir at a predetermined rate of between about 20 ml./min. and 200 ml./min.

* * * * *